US010169931B2

(12) United States Patent
Remboski et al.

(10) Patent No.: US 10,169,931 B2
(45) Date of Patent: Jan. 1, 2019

(54) SERVICE IMPROVEMENT BY BETTER INCOMING DIAGNOSIS DATA, PROBLEM SPECIFIC TRAINING AND TECHNICIAN FEEDBACK

(71) Applicants: Donald Remboski, Ann Arbor, MI (US); Assi Bitton, Rosh Haayin (IL); Yoav Megged, Rosh-Haayin (IL); Jacqui Dedo, Wolverine Lake, MI (US); Dani Shafriri, Rosh-Haayin (IL)

(72) Inventors: Donald Remboski, Ann Arbor, MI (US); Assi Bitton, Rosh Haayin (IL); Yoav Megged, Rosh-Haayin (IL); Jacqui Dedo, Wolverine Lake, MI (US); Dani Shafriri, Rosh-Haayin (IL)

( * ) Notice: Subject to any disclaimer, the term of this patent is extended or adjusted under 35 U.S.C. 154(b) by 23 days.

(21) Appl. No.: 15/404,308

(22) Filed: Jan. 12, 2017

(65) Prior Publication Data

US 2018/0197354 A1 Jul. 12, 2018

(51) Int. Cl.

| | |
|---|---|
| ***C07C 5/00*** | (2006.01) |
| ***G07C 5/08*** | (2006.01) |
| ***G07C 5/00*** | (2006.01) |

(52) U.S. Cl.
CPC ........... *G07C 5/0808* (2013.01); *G07C 5/008* (2013.01); *G07C 5/0816* (2013.01)

(58) Field of Classification Search
CPC ....... G07C 5/00; G07C 5/0808; G07C 5/0816
See application file for complete search history.

(56) References Cited

U.S. PATENT DOCUMENTS

| | | | | |
|---|---|---|---|---|
| 7,089,099 | B2 * | 8/2006 | Shostak | B60C 23/005 701/29.6 |
| 7,103,460 | B1 * | 9/2006 | Breed | B60C 23/0408 701/29.1 |
| 7,421,321 | B2 * | 9/2008 | Breed | B60C 11/24 340/442 |
| 9,043,073 | B2 * | 5/2015 | Ricci | G06F 17/00 340/438 |
| 2005/0192727 | A1 * | 9/2005 | Shostak | B60C 11/24 701/37 |
| 2005/0273218 | A1 * | 12/2005 | Breed | B60C 11/24 701/2 |
| 2006/0025897 | A1 * | 2/2006 | Shostak | B60C 23/005 701/1 |
| 2015/0161893 | A1 | 6/2015 | Duncan | |
| 2015/0228129 | A1 | 8/2015 | Cox | |

* cited by examiner

*Primary Examiner* — Yonel Beaulieu
(74) *Attorney, Agent, or Firm* — Reches Patents

(57) ABSTRACT

A method for failure analysis and technician assessment, the method may include
sensing sensed vehicle parameters by multiple vehicle sensors that comprise multiple types of sensors; calculating, by a vehicle monitor, based on the sensed vehicle parameters, parameters of multiple vehicle components; wherein the vehicle monitor is mechanically coupled to the vehicle or installed in the vehicle; searching, by the vehicle monitor and based on the parameters of the multiple vehicle components, for a vehicle failure that is either a current vehicle failure or an impeding vehicle failure; receiving, by the vehicle monitor, a notification that the vehicle failure was repaired; and estimating an impact of the repair by the vehicle monitor and based on at least parameters of multiple vehicle components that are calculated from sensed vehicle parameters that are sensed after the repair.

24 Claims, 25 Drawing Sheets

300

500

502

600

2100

5200

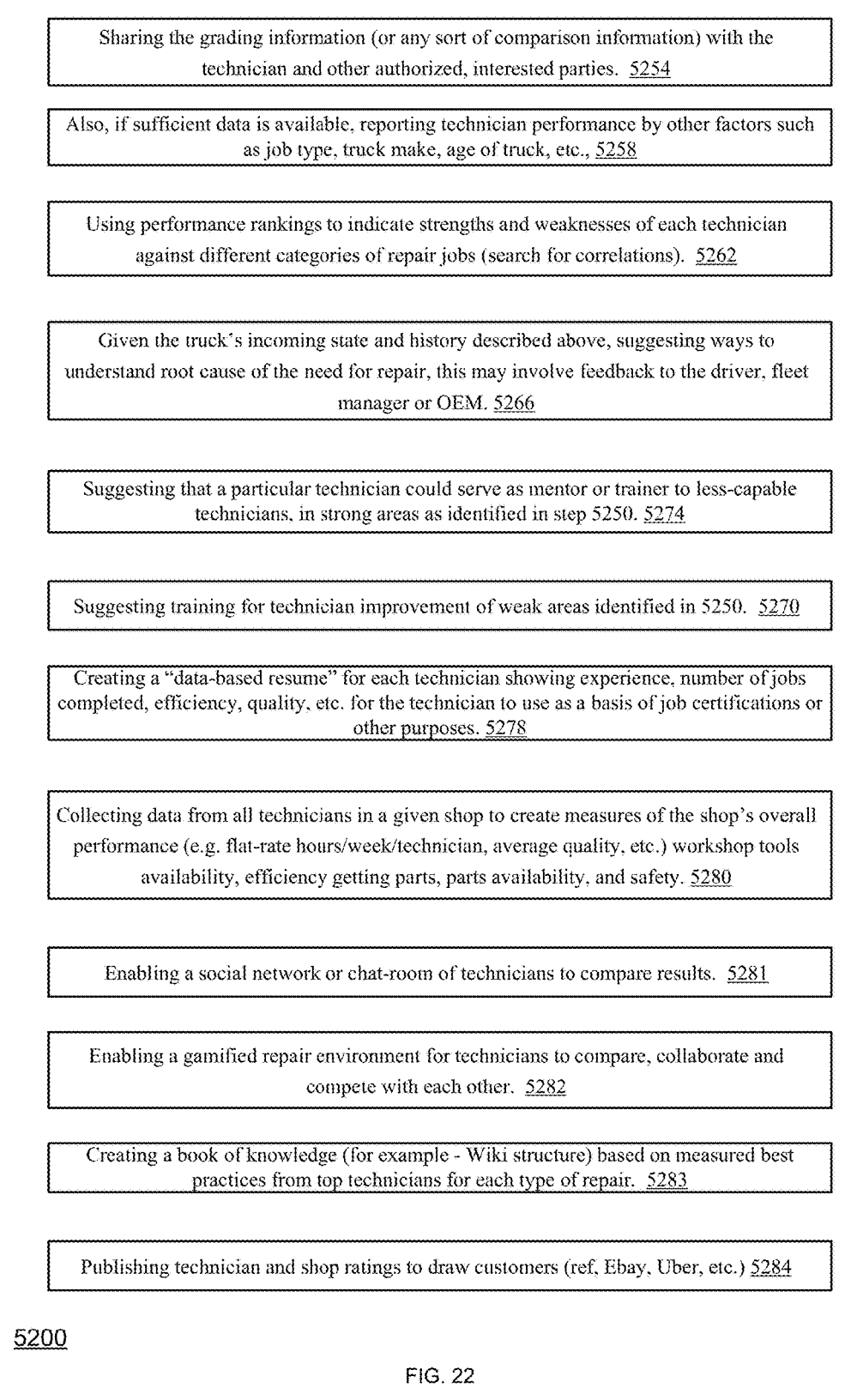

Sharing the grading information (or any sort of comparison information) with the technician and other authorized, interested parties. 5254

Also, if sufficient data is available, reporting technician performance by other factors such as job type, truck make, age of truck, etc., 5258

Using performance rankings to indicate strengths and weaknesses of each technician against different categories of repair jobs (search for correlations). 5262

Given the truck's incoming state and history described above, suggesting ways to understand root cause of the need for repair, this may involve feedback to the driver, fleet manager or OEM. 5266

Suggesting that a particular technician could serve as mentor or trainer to less-capable technicians, in strong areas as identified in step 5250. 5274

Suggesting training for technician improvement of weak areas identified in 5250. 5270

Creating a "data-based resume" for each technician showing experience, number of jobs completed, efficiency, quality, etc. for the technician to use as a basis of job certifications or other purposes. 5278

Collecting data from all technicians in a given shop to create measures of the shop's overall performance (e.g. flat-rate hours/week/technician, average quality, etc.) workshop tools availability, efficiency getting parts, parts availability, and safety. 5280

Enabling a social network or chat-room of technicians to compare results. 5281

Enabling a gamified repair environment for technicians to compare, collaborate and compete with each other. 5282

Creating a book of knowledge (for example - Wiki structure) based on measured best practices from top technicians for each type of repair. 5283

Publishing technician and shop ratings to draw customers (ref, Ebay, Uber, etc.) 5284

5200

FIG. 22

SERVICE IMPROVEMENT BY BETTER INCOMING DIAGNOSIS DATA, PROBLEM SPECIFIC TRAINING AND TECHNICIAN FEEDBACK

RELATED APPLICATIONS

This patent application claims the priority of U.S. provisional patent Ser. No. 62/277,976 filing date Jan. 13, 2016, U.S. provisional patent Ser. No. 62/277,977 filing date Jan. 13, 2016, U.S. provisional patent Ser. No. 62/277,981 filing date Jan. 13, 2016, U.S. provisional patent Ser. No. 62/277,982 filing date Jan. 13, 2016, and U.S. provisional patent Ser. No. 62/277,988 filing date Jan. 13, 2016, all are incorporated herein in by their entirety.

BACKGROUND

There is a growing need to provide improvements in the fields of vehicle monitoring, application approvals, service improvement, product improvements, failure analysis and warranty claim assessment, and new feature launch.

SUMMARY

Systems, vehicle monitors, methods and computer program products as illustrated in the specification and/or claims.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 22 illustrates a method according to an embodiment of the invention;

DETAILED DESCRIPTION OF THE DRAWINGS

Figure 1:
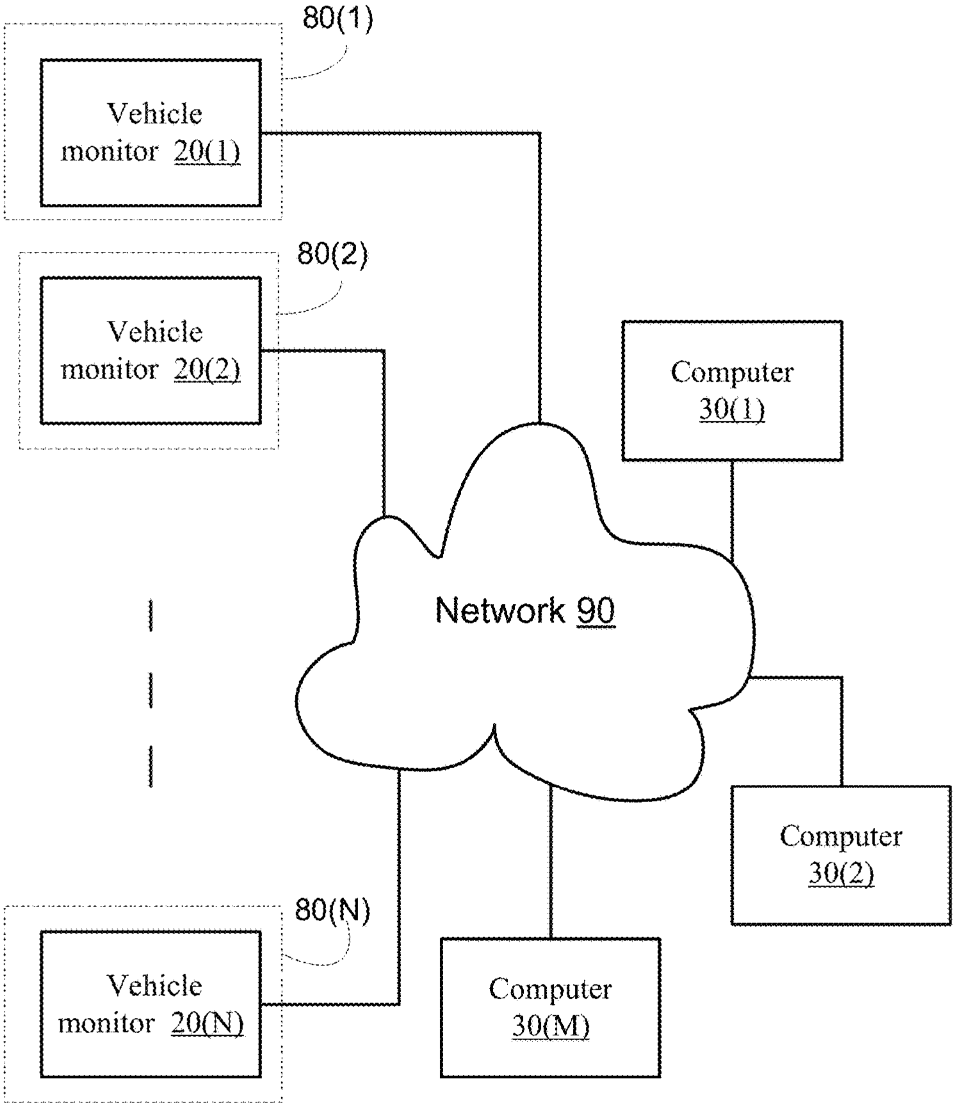
FIG. 1 illustrates a system and its environment according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The terms "computer program product" and "computer readable medium" are used in an interchangeable manner and can replace each other.

The phrase "and/or" means additionally or alternatively.

Any reference to "comprising" or "comprises" or "includes" or "including" should be interpreted as also applying to "consisting" and/or to "consisting essentially of". For example—a method that is illustrated as including certain steps may be limited only to these steps, may have additional steps or may have additional steps that do not materially affect the basic and novel characteristic(s) of the method.

The terms "truck" and vehicle are used in an interchangeable manner and can replace each other. Accordingly—any reference to a truck or a vehicle should be applied to trucks as well as other vehicles such as buses, cars, marine vehicles, and the like.

The terms "vehicle monitor" and "telematics system" are used in an interchangeable manner and can replace each other. A non-limiting example of a telematics system is the telematics system of Traffilog Israel. The vehicle monitor may be a part of a telematics system or may be the telematics system itself.

The terms "vehicle system parameter", "vehicle component parameter" are used in an interchangeable manner—and one term can replace the other.

Any combination of any steps of any of the method illustrated in the drawings and/or the specification can be provided.

A vehicle monitor capable of executing any combination of any steps of any of the method illustrated in the drawings and/or the specification can be provided.

Any but width, size, frequency, number are provided only as an example. Any example in the specification is a non-limiting example.

Accurate Application Approval

The term application means recommendations, suggestions and/or instructions about how a customer will use a particularly configured vehicle.

Vehicle original equipment manufacturers (OEMs) typically should approve applications before a vehicle can be sold.

There applications provided by vehicle OEMs are based on duty cycles.

There is a growing need to provide accurate duty cycle measurements.

There are provided systems method and computer program products for evaluating vehicle configurations when the vehicle is operated according to a given application (also referred to as "application of interest"). The evaluating is done in a reliable manner, based on duty related parameters of multiple vehicle components.

The method can be executed (fully or in part) by a vehicle monitor that is mechanically coupled to the vehicle and/or is installed in the vehicle.

The vehicle monitor may process a vast amount of information—especially a vast amount of sensed vehicle parameters. These sensed vehicle parameters may be sensed by multiple vehicle sensors. The vehicle sensors may be included in the vehicle and/or mechanically coupled to the vehicle. The vehicle sensors may include multiple types of sensors.

For example a truck can be monitored by tens and even more than hundred sensors. For example—engine/after treatment sensors—between 20 to 30 sensors; transmission sensor (automated and/or manual)—between 7 to 10 sensors, driveline sensors (tandem axle) between—4 to 6 sensors; brakes sensors (tandem axle, disc brake)—between 21 to 24 sensors; Tires/Wheels sensors—12 sensors; high voltage supply (HVAC) sensors—between 4 to 6 sensors; telematics/Infotainment/Navigation—6 sensors, Body/Lighting sensors—between 8 to 10 sensors; ADAS—between 6 to 10 sensors and trailer sensors—between 6 to 8 sensors—totals 88 to 122 sensors. The different number of sensors may result from regional differences because of emissions and safety regulation.

This vast amount of information could not be transmitted from the vehicle to a remote computer located outside of the vehicle because of bandwidth constraints and/or because of lack of reception in various regions in which the vehicle travels. Alternatively—the cost associated with the transmitting the vast amount of information would render the transmission too costly.

The vehicle monitor may be configured to determine, based on the sensed vehicle parameters, duty related parameters of multiple vehicle components.

The vehicle monitor may also be configured to calculate the performance of the vehicle when configured according one or more vehicle configurations—when the vehicle is operated according to a given application.

The calculation of the performance of the vehicle may be based on, at least, (i) the duty related parameters of the multiple vehicle components and (ii) relationships between the duty related parameters of the multiple vehicle components and the performance of the vehicle.

Alternatively, the vehicle monitor or another vehicle transmitter may transmit the duty related parameters of the multiple vehicle components towards a receiver located outside the vehicle and the duty related parameters of the multiple vehicle components may be processed by a system or computer such as a remote computer (a computer that is not included in the vehicle).

The remote computer may calculate the performance of the vehicle, and the calculation can be based on, at least, (i) the duty related parameters of the multiple vehicle components and (ii) relationships between the duty related parameters of the multiple vehicle components and the performance of the vehicle.

The aggregate size of the duty related parameters of the multiple vehicle components is a fraction (for example less than 1/100 or 1/1000 or 1/10000 of 1/1,000,000) of the aggregate size of the sensed vehicle parameters. The duty related parameters may reflect S—N curves of components that are subjected to cyclic fatigue failure or may be any compressed representation of the sensed vehicle parameters. For example—a single duty related parameter may represent the values of sensed vehicle parameters over a period of time.

Due to the size difference the transmission of the duty related parameters of the multiple vehicle components is cost effective and does not impose unreasonable limits of the bandwidth.

It should be noted that the vehicle monitor may evaluate the performances of multiple vehicles configurations (when the vehicle is operated according to the given application) and may select a particular vehicle configuration. The selection may be based on the performances of the vehicle configurations and on the given application.

The selection can be made by the remote computer.

The monitoring and/or calculation of the duty related parameters of the multiple vehicle components provides a real estimate of the actual application (the actual manner in which the vehicle is used by a client) and may be used for selecting the vehicle configuration that may fit that given application.

Typically, vehicle buyers tend to underestimate the duty of their vehicles undergo (are too optimistic regarding the application) and vehicle OEM tend to overestimate the duty that their vehicles undergo. The monitoring and/or calculation of the duty related parameters provides a real estimate of the load that is undergone by the vehicle, and this real estimate may assist both parties in finding the vehicle configuration that will best match the actual application.

Accordingly—vehicle OEMs can improve the product/part selection, accuracy and speed of application approvals by using measured duty cycle data from the given application.

This benefits vehicle OEMs by having greater certainty that the approved vehicle will perform well in the given application. This benefits the vehicle buyer by assuring that the vehicle is neither over-specified or under-specified and is, therefore, the most cost-effective solution.

OEMs can also improve the speed of application approval by implementing this concept with an online facility for analyzing applications (e.g. web site with help desk, to be used by the vehicle salesman).

This analysis can also offer vehicle users an accurate estimate of fuel economy, vehicle durability and other performance parameters of interest. This further analysis assists vehicle users in selecting the optimal vehicle for their application and in modeling out how their business will perform when using a particular vehicle.

This capability also opens up new business models by including financing options and warranty coverage options as part of the application approval.

There is a provided a system, method and computer readable medium that is configured to determine (a) if an application is approvable, (b) if an application meets customer needs for payload, fuel efficiency and other factors, and/or (c) if an application is otherwise optimal (e.g. in the sense of maximizing weighted utility functions for all parameters of interest), The relationships between the duty of the vehicle (or duty of components of the vehicle and/or duty of different systems of the vehicle) and the performance of the vehicle can be represented in various manners, such as but not limited to a performance model of the vehicle.

The performance model of the vehicle may be generated based on analyzing data from at least some of the following sources:

a. OEM system and sub-system durability data or usable life estimates generated by engineering analysis and laboratory testing.

b. Monitoring system supplied, field empirical, system and sub-system durability data or usable life estimates generated by comparing wear-out and repair history to vehicle duty.

c. A list of plausible vehicle configurations or vehicle configurations acceptable to the customer.

d. After sales inputs by using the system and by after sales external data like: Real Parts mean time between failure MTBF. Customer real missions. Real shop downtime. Aftermarket users (parts MFRSs) to demonstrate parts durability. Aftermarket sources of component data for common parts.

The performance model of the vehicle may be generated by at least one of the following:

a. Analysis methods for combining analytical, laboratory or empirical field data and OEM and user targets for application performance to produce application performance models.

b. Statistical correlation methods (e.g. linear regression, regression against a non-linear function), c. Physics-based simulation methods where a physical model is calibrated using analytical, laboratory or field empirical data, d. Using optimal observers to correlate or calibrate steps a or b above.

The system performance model may run with the measured duty to produce ratings of the different configurations against OEM and customer needs (e.g. projected warranty cost, projected down time, projected fuel efficiency, etc.).

Multiple configuration may be evaluated.

The multiple configurations may be provided in at least one of the following manners:

a. Manual modification of configurations, where the user is in the loop changing configurations to seek better results.

b. Automated modification of configurations using Monte Carlo, partial derivative optimization or other techniques to seek better results.

c. Massive parallel analysis of all possible configurations and subsequent sorting/searching for optimal configurations.

As indicated above, the method may be executed by the vehicle monitor alone or by both the vehicle monitor and a remote computer.

The vehicle monitor is installed in a vehicle (or coupled to the vehicle) and is configured to sense, compute, provide a user-interface. The vehicle monitor may include a computer, one or more sensors and a communication unit. The computer runs software that observes sensors computes parameters of interest based on sensor observations (sensors may be part of the vehicle or added on after the vehicle is manufactured).

Parameters of interest are then used directly or combined mathematically and then used in the following ways:

a. To trigger an event such as: an alarm, a modification of data collection methods, a transmission of collected data, or a number of other actions, b. Averaged or filtered to produce a lower bandwidth signal or reduce out of band noise.

c. Stored in local memory.

The vehicle monitor may execute software that may include a real-time operating system with hardware support and a dynamically re-programmable application layer. The back-office computing system manages versioning and download of both real-time operating system and the dynamic application layer.

The vehicle monitor may include a communication unit and/or be coupled to a communication unit such as such as a cellular data communication unit and/or an Internet data communication unit—that allows data communication between in-vehicle platform and other entities such as a back-office facility. The communication unit of the vehicle monitor can connect directly with a mobile network, satellite network or any wireless network.

Additionally or alternatively, the communication unit may communicate (by short range communication) with a unit of the vehicle (such as a multimedia center, radio, or any unit that is installed in the vehicle—such as the smartphone of communication unit of a driver of the vehicle). The unit of the vehicle may communicate with the mobile network, satellite network or any wireless network.

The remote computer is not a part of the vehicle and may include, for example, a back-office computing, data storage system, and proactive call center—runs offline and near-real time applications to provision in-vehicle units, analyze data from in-vehicle units, store data from in-vehicle units and analysis, create reports, host web applications, etc. The call center both notifies customers of problems and receives calls from customers with questions. The back-office computing may by any type of computer and may include one or more servers, one or more desktop computers, one or more laptop computers, a mobile device, and the like. The other computer may be located within a cloud computerized environment.

The vehicle monitor may have a campaign structure, and can provide better information by measuring both long-term steady-load conditions and by capturing short-term high-load (overload, damage-cycle) information. Any of the vehicle monitors illustrated in the specification may or may not have a campaign configuration.

A campaign configuration is the ability of the vehicle monitor to collect, categorize and report machine data related to a particular aspect of the machine's operation (vehicle parameters, vehicle component parameters, vehicle system parameters).

These aspects may include, for example, maintenance, wear-state of the machine, hydraulic usage, overall machine duty and many others. Data feeds into the campaign structure from multiple sources (sensors, computed values, data from other ECUs) and at high data rates.

For some sensors, such as GPS, this could be as low as 10 samples/sec. Most sensors, related to engine, transmission and suspension (accelerometers, vibration, shaft angular displacement) will need to be sampled at 10000 samples/sec or higher rates. For 16-bit data, which is typical, this amounts to 144 GB per year of data for each sensor monitored (2000 hours of operation per year).

A typical installation will require monitoring ten different sensors, which generates 1.4 TB of data per year per truck. For a 1000 truck fleet this is 1.4 PB of data. Data is then categorized and accumulated to produce an overall view of some aspect of the machine's operation. For example, over the course of operation, a truck's suspension may undergo millions of stress cycles.

Each stress cycle is measured by high-bandwidth sensors (e.g. accelerometers) sampled 10000 times a second. This data is reduced to a single parameter indicating the peak magnitude of the stress cycle. This parameter is then categorized by size and then an accumulator of similar sized stress cycles is incremented. This data reduction step reduces the data size by seven orders of magnitude or more. The resulting stress cycle accumulators are transmitted to the infrastructure and are used to categorize the suspension duty and wear-state.

In this example, the stress cycle accumulator may have 100 buckets (stress ranges), each of which would be a 32-bit integer.

If the accumulator is transmitted once per day this is 400 B per day or 20,800 B per year, which is a large reduction over the 144 GB/year for unprocessed data (7,000,000:1). This data includes of one hundred 32-bit counters each of which indicates how many times a given peak stress level was achieved for a particular small range of stress values. The smallest stress level range "bucket" to the largest stress level range spans the range of stress levels seen in the field.

In other examples, data reductions by means other than peak detection are required. We may use high-bandwidth sensor data to perform an ongoing calibration of a computer model intended to predict a system behavior of interest. In a simple, case this could be a best fit line to match the incoming data from a sensor, sampled 10000 times a second, calculated every minute. This reduces the data rate from 1.2 MB per minute to 6 B per minute (16 bit values of line slope, line intercept and a 16-bit goodness of fit indicator such as R-squared).

For example, the data collection and categorization process can take a number of forms such as:

a. Simple digital input events—accumulate the total time of digital input, average duration of digital inputs, number of digital inputs events, or vehicle distance traveled during digital input. Also accumulate digital inputs logically combined with count, time or distance traveled parameters. For example: count the number of times the brake is pressed, the number of times the brake is pressed more than 10 seconds, or the number of times the brake is pressed in a day.

b. Combined digital events—Form and accumulate a logical combination of the above simple digital events with the logic operators AND, OR and NOT. Also accumulate combined digital events logically combined with count, time or distance parameters.

c. Analog Parameter Statistics—Accumulate common statistics (mean, median, standard deviation, distribution and density). Combine statistics and pre-defined constants using relational operators ($<$, $>$, $=$, $\leq$, $\geq$, $\neq$) to create digital events that can be used as described above.

d. Analog Parameters Statistics Between Periods—Compare analog parameter statistics between different pre-defined periods of time using methods as described above. For example, count the number of times that the average daily engine oil pressure is more than 1 bar lower than the previous day.

e. Analog Parameters Statistics Between Vehicle Type Groups—Compare analog parameter statistics between pre-defined vehicle groups using methods described above.

Traditional vehicle monitors measure only a few vehicle parameters, such as DTC status, vehicle location or vehicle speed. Measurements are made at a low repetition rate. These few parameters are sent via a cellular data channel to the cellular service provider's storage facility. Analysis of the data is made in a non real-time manner for the preparation of reports.

By contrast the suggested vehicle monitor measures nearly all vehicle parameters at whatever repetition rate is required to learn the system behavior.

Further the suggested vehicle monitor can combine parameters to deduce system states that are not measured directly.

Depending on the needs of a particular measurement situation, the suggested vehicle monitor can process data in real-time on the truck or in near-real time in the back office. This allows the suggested vehicle monitor to measure parameters at a high rate, make analysis locally in the truck and then send relatively small amounts of data over cellular channels. This reduces the cost of cellular data transmission while insuring that all of the relevant data is captured.

The suggested vehicle monitor also stores background data on component performance and life to assist the OEM in calibrating a system/component life model used to estimate component life for each truck configuration being investigated. See the drawing below for one possible embodiment of the invention.

The suggested vehicle monitor maintains a detailed history of how a particular vehicle has been used. By comparing this detailed use history to known component failures and known repair history the vehicle monitor provides OEMs with a knowledge base of component life. This knowledge base can then be used to calibrate component life models used in product design and application approval.

FIG. 1 illustrates multiple vehicle monitors 20(1)-20(N) of vehicles 80(1)-80(N) respectively. The multiple vehicle monitors 20(1)-20(N) provide information, via network 90, to a computerized system (illustrated as including multiple computers 30(1)-30(M)) that participate in the evaluation of the application. In this configuration, information about each individual vehicle and about the composite performance of all vehicles is available for analysis. This configuration also allows optimal use of computing resources and optimal use of data communication service. Alternatively, the analysis is done, partially or fully by the vehicle monitors themselves. The vehicle monitors may form a distributed network of computers that may perform the analysis in a distributed or centralized manner. For example—one vehicle monitor may analyze information supplied by another vehicle monitor. Load balancing techniques may be applied between the vehicle monitors.

Figure 2:
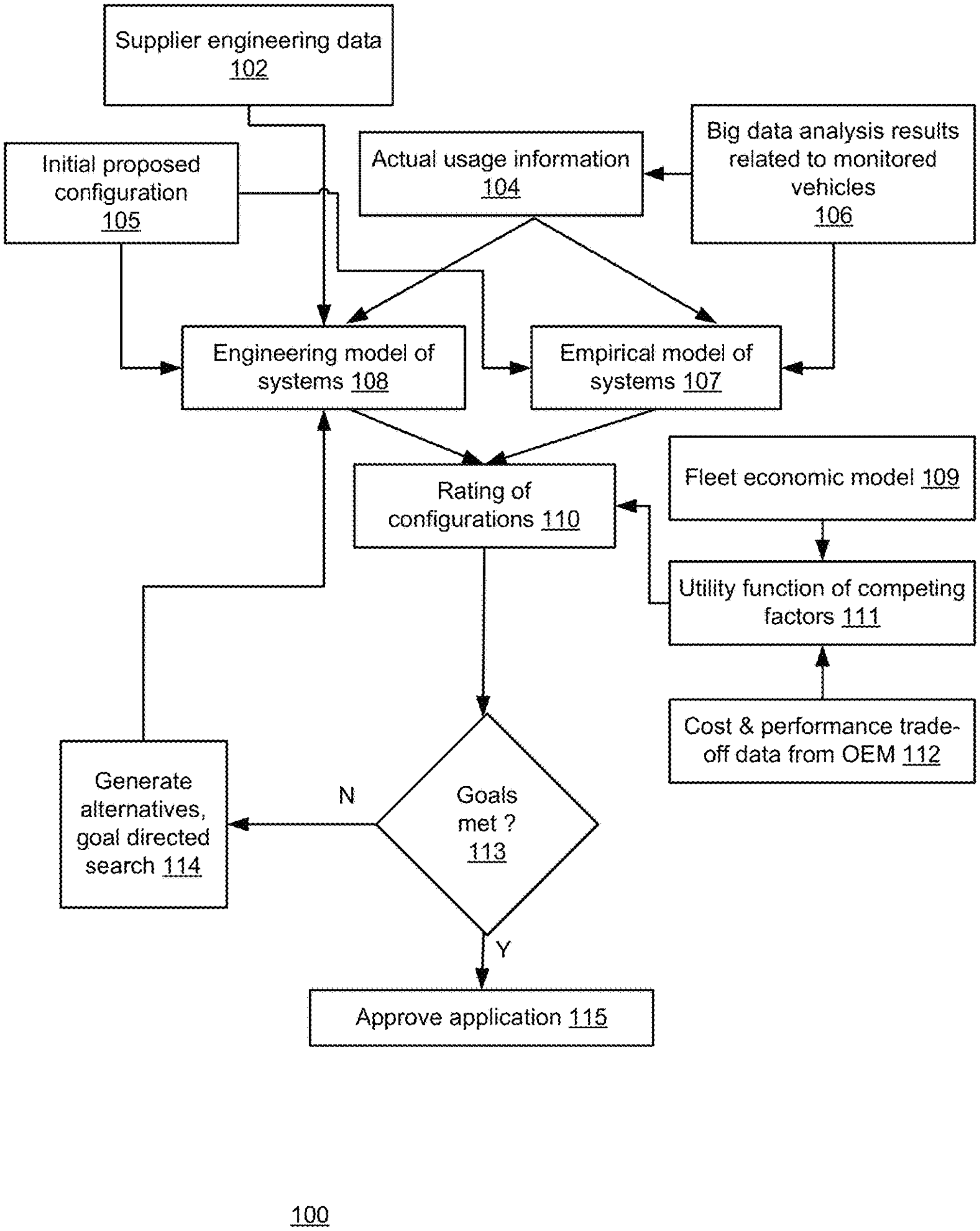
FIG. 2 illustrates a method according to an embodiment of the invention.

FIG. 2 illustrates a method 100 according to an embodiment of the invention.

Method 100 may include:

a. Step 102 of gathering supplier engineering data such as test-bench derived S—N curves or ultimate strength limits for components of interest.

b. Step 104 of gathering actual usage information for an application of interest (for example duty related parameters such as annual ton-miles hauled, average engine load, or peak engine load).

c. Step 106 of processing actual usage information (gathered during step 104) from vast number of measurements of vehicle monitors using big data technique to provide big data analysis results. In particular, we are looking for correlations between any of the measured parameters and the performance of a component of interest to create an empirical predictive engineering model of the component's performance. We also analyze the big data to calculate the truck state parameters that are not directly measured. For example, the total energy dissipated in the brakes is not directly measured, but is calculated from truck speed, truck altitude and brake actuation data pulled from the big data set.

d. Processing (step 108) the big data analysis results, the supplier engineering data and initial proposed configurations (gathered in step 105) by an engineering model of vehicle systems. The engineering model of a system relates usage of the system to the system's performance, in particular, to the system's degradation with time. For example, in a mechanically stressed component, this model relates the number of stress cycles to the probability of component failure.

e. Processing (step 107) the big data analysis results by an empirical model of the system. For example, this may be done by making a study of correlations between usage and component performance data to find relationships between vehicle usage and component performance.

f. Step 109 of gathering data describing a fleet's economic model and using this data to rank and proportion different competing economic factors (e.g. by understanding the tradeoff between fuel cost vs. driver pay vs. cost of capital, we can understand what is the optimal truck in terms of fuel efficiency, fuel efficiency degradation at higher speeds and vehicle cost, all of which can be calculated from the engineering and empirical models).

g. Rating (step 110) configurations based on the outcomes of steps 107, 108 and 111. System performance from steps 107 and 108 are scaled by utility functions from step 111 and added up to provide rankings of the different configurations. The ratings are a comparison of projected system performance against OEM and customer goals. For example, an OEM may have a 500,000 mile durability goal for a given system. If the system model, when run against the customer's duty cycle for 500,000 miles, predicts a system failure then the application receives a low rating.

h. Step 111 includes applying a utility function of competing functions on fleet economic model (gathered in step 109) and on cost and performance trade off data from OEM (step 112). This utility function determines the optimum balance between directly competing goals between vehicle OEMs and fleets (e.g. vehicle price, OEMs want a higher price, fleets want a lower price). The utility function also sets diminishing-returns limits on non-competing goals (e.g. improved reliability is generally beneficial to OEMs and fleets, but only up to the point that it improves OEM pricing or reduces fleet operating costs).

i. The outcome of step 110 is fed to decision step 113 of checking if goals are met and if so—the application is approved (step 115).

j. Else—step 113 is followed by step 114 of generating alternative applications, goal directed search and jumping to step 108.

k. Goals used in step 113 are supplied by OEMs and customers. For example, an OEM may have a goal of 500,000 miles component useful life. If the analysis indicates that a component does not have 500,000 miles useful life when used as the customer intends, the goal is not met. Customers may have goals related to cost of operation or frequency of maintenance and repairs. The goal generation may feed the rating of configurations.

l. Step 114 generates new system configurations to evaluate when goals are not met with previous system configurations. For example, we can generate new truck configurations using the OEM truck configuration software that validates major component selections such as engines, transmissions, drivelines, brakes and axles.

m. New configurations can be generated in a number of ways including: user directed changes to configurations, randomly generated changes to configurations, or analytically, goal directed, changes to configurations (e.g. finding maxima of ratings by analysis of partial derivatives of ratings with respect to inputs).

The steps of method 100 may be de-serializing using mass analysis techniques.

Method 100 may be executed by a computer, a vehicle monitor, and the like.

Figure 3:
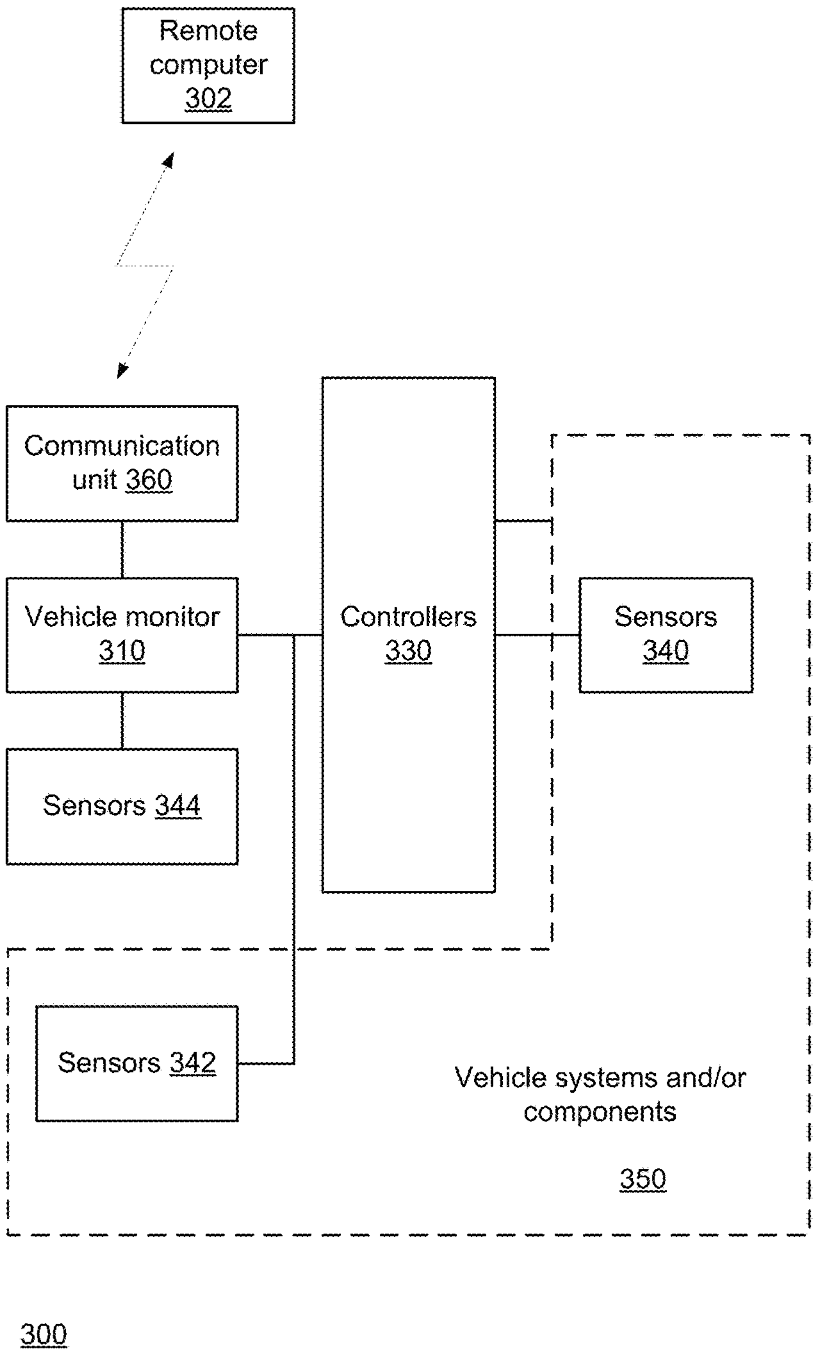
FIG. 3 illustrates a vehicle according to an embodiment of the invention.

FIG. 3 illustrates a vehicle 300.

The vehicle 300 includes vehicle monitor 310, communication unit 360, controllers 330, and sensors 340, 342 and 344 as well as vehicle systems and/or vehicle components 350.

Sensors 344 are coupled to the vehicle monitor 310 but not to controllers 330. Sensors 330 are coupled to controllers 330 but not to vehicle monitor 310. Sensors 342 are coupled to vehicle monitor 310 and to controllers 330. Any combination of couplings between sensors and other units/modules may be provided.

The controllers 330 are configured to control various vehicle systems. A single controller may control a single vehicle system—but this is no necessarily so and one controller can control multiple vehicle systems and/or multiple controllers can cooperate to control a single vehicle system.

Non-limiting examples of vehicle systems include engine, transmission, brakes/antilock brakes, electronic stability control, axle/driveline, suspension/ride height control, tires/tire inflation monitor/control, instrument panel/driver interface.

Sensors 340, 342 and 344 may include at least some out of the following controllers: ambient air temperature sensor, absolute pressure sensor, tire pressure sensor, tire temperature sensor, wheel speed sensor, propeller shaft speed sensor, engine speed sensor, engine coolant temperature sensor, engine coolant pressure sensor, engine oil pressure sensor, engine oil temperature sensor, engine inlet air temperature sensor, engine inlet air pressure sensor, engine inlet air temperature sensor, engine exhaust temperature sensor, engine exhaust pressure sensor, 3-axis chassis acceleration, steering sensor, braking sensor, throttle position sensor, ride height sensor, suspension inflation pressure sensor, clutch sensor, height sensor, location sensor (GPS), and the like.

Vehicle monitor 310 may receive sensor data from sensors 322 and 334. Vehicle monitor 310 may receive from controllers 330 sensor data (from sensors 330 and/or 332) and/or may receive computed values from controller 330. The processed data and/or the sensor data may include duty related parameters.

An example of sensor data that may be provided from controllers 330 may include, for example, engine coolant temperature or engine revolutions per minute (RPM). Examples of the computer data may include engine torque, engine power, and engine fuel rate that are calculated by the controllers 330 based on mathematical combinations of sensor data.

The communication unit may be configured to perform short range communication (especially within the vehicle) and/or long range communication (especially between the vehicle and networks located outside the vehicle). The long and short communication may be managed by different communication units of the vehicle. For example—the vehicle monitor may include a short range communication unit that wirelessly (or in a wired manner) communicates with another communication unit of the vehicle that may also manage long range communication.

Vehicle monitor 310 may include a processor, a memory unit and multiple communication ports. The processor may be a general purpose processor, a digital signal processor, a FPGA, a microcontroller, and the like. For example, the processor may include a low power micro controller unit of ST microelectronics.

The vehicle monitor may measure the actual duty of the application of interest. The actual duty may be reflected by duty related parameters of multiple vehicle components. The vehicle components may be include in any of the vehicle systems and may include, tires, chassis components, engine components, and the like. A vehicle component may be mechanical components, and electrical component or any other component of the vehicle.

The actual duty of the vehicle may be measured directly from sensors with simple (meaning directly measured from a physical-parameter-to-voltage transducer) parameters such as: vehicle mileage, amount of time at a power level (histogram of time vs. power), amount of mileage at a specific load (histogram of mileage vs. load), amount of time on at a given level of road roughness (RMS measure of vertical acceleration) and other directly measured quantities.

These measurements are made using sensors commonly fitted (many sensors are commonly fitted on vehicles today for reasons other than telematics measurements, e.g. inlet air pressure, inlet air temperature are used to control fueling rate on engines) on vehicles such as odometers, accelerometers and using data from the engine's electronic control unit (e.g. engine speed, engine load). These parameters are measured, recorded, and stored by the vehicle monitor. These sensors commonly supply data via CAN bus messages.

It should be noted that the terms "CAN", "CANBUS" and "CAN bus" are used in an interchangeable manner.

In addition to this, the actual duty of the vehicle is also estimated by combining measured parameters and mathematical engineering models of the vehicle's hardware.

In the example that follows, the vehicle monitor combines vehicle speed, vehicle altitude, engine torque with brake actuation/retarder actuation command information to form a measure of energy dissipated in the brakes or retarder.

For example, accumulated brake system energy dissipation is a measure of brake duty. Brake system energy dissipation is determined by observing the change in the vehicle's total (potential and kinetic) energy before and after a braking event, then subtracting to form the difference in energy.

The energy difference is due to braking effort. The braking effort energy of each braking event that the vehicle undergoes is added to an accumulator that holds the measure of total energy dissipated by the brakes for all braking events.

The vehicle's change in kinetic energy is calculated using an estimate of the vehicle's mass and the vehicle's measured speed before and after the braking event (KE=½mvˆ2).

The vehicle's change in potential energy is calculated from the vehicle's mass and the change in altitude the vehicle underwent during the braking event (PE=mgh).

The vehicle's mass is typically estimated by the transmission controller and the vehicle's change in altitude is measured by a global positioning system {GPS} altimeter (also referred to as "GPS unit"). In applications that have the possibility of engine braking or retarders, the energy absorbed by these devices also needs to be considered, both on their own as components and as offsets to the energy dissipated in the brakes. The deployment of brakes, engine brake or retarder is known from CAN bus messages describing the braking event.

For example, in some ways similar to the brake energy example above, the vehicle monitor can estimate overall engine duty by measuring the amount of work that the engine has done in total and in between maintenance events. This is conveniently measured as kilowatt-hours and has the units of energy.

Measure the engine power, in kilowatts, every second (kilowatt seconds), multiply by 3600 to get kilowatt-hours. Add this value to an accumulator keeping the engine's total kilowatt-hour total.

The vehicle monitor can also measure how much energy is produced at a given power level (work rate) to account for accelerated engine wear at high power levels. In this case, the vehicle monitor can keep an ongoing tally of time at a given power level (bucketed into small ranges of power). This data can then form a histogram that shows the amount of time at a given power level. The area under each bar in the histogram is energy produced at that power level. Engine wear increases dramatically when operated at high power levels. The time-at-power histogram gives a good picture of the engine's wear state. In this case, the engine's electronic control unit supplies engine speed, torque and power measurements.

For example, for manual transmission, to gain an accurate understanding of transmission duty, the vehicle monitor may need to measure the amount of energy that the engine has put into the transmission in total and separately for each gear range available in the transmission. To do this the vehicle monitor continuously observes the engine's output power (supplied by a controller such as engine control unit {ECU} over the CAN bus), the gear range of the transmission (supplied by a controller such as the transmission control unit {TCU} over CAN bus), clock time and if the clutch is open or closed (supplied by clutch switch directly to vehicle monitor).

The vehicle monitor takes this information and accumulates the amount energy produced by the engine (kilowatt-hours as described above) for a total transmission energy measurement. The vehicle monitor also maintains a separate accumulator for engine energy put into the transmission for each transmission gear range.

For example, to gain an accurate understanding of clutch duty the vehicle monitor may measure the total energy deposited in the clutch during engagement and disengagement actions. The amount of energy deposited in the clutch is the amount of power lost in the clutch multiplied by the time interval of the observation: (input power–output power)*time interval.

This is proportional to (input speed–output speed) *torque*time interval (Here's why: input power=input speed*input torque, output power=output speed*output torque, torque is the same on input and output therefore power lost in the clutch is proportional to the speed difference across the clutch times torque).

The input speed to the clutch is engine speed as supplied by the ECU via CAN bus.

The output speed of the clutch is derived from the road speed of the vehicle adjusted for tire circumference, final drive (axle) ratio, and transmission ratio for the current gear. Output speed (rev/min)=Road speed (mile/hour)*tire circumference (rev/mile)*hour/60 minutes*final drive ratio*transmission ratio for current gear For example, for suspension components subject to cyclic variations in load, but not force reversals, the vehicle monitor may accumulate the number of and magnitude of force fluctuations in the suspension. The vehicle monitor may first calculate the static force on the suspension from an estimate of vehicle mass supported by the suspension and then add to this the force of upwards accelerations of the vehicle as measured by an accelerometer.

This accelerometer responds in a positive sense to vehicle upwards accelerations due to road roughness. These accelerations, times the supported mass, is the additional force on the suspension due to road roughness (F=ma).

The vehicle monitor accumulates a count of fluctuations, bucketed into small ranges of force, for every force fluctuation observed in the suspension. The resulting histogram of number of events at a given force level is an indicator of suspension duty. (Later the vehicle monitor may will use this data, an S—N curve of the component, and Miner's Rule to predict life of components subject to this duty.)

For determining engine efficiency, the vehicle monitor may need to accumulate an engine "time at speed vs. torque map." In this map, the vehicle monitor may accumulate the amount of time of engine operation at every engine speed and engine torque (bucketed into small bands of speed and torque). This data is used in conjunction with an engine BSFC map (described below) to estimate fuel consumption of different engines/driveline combinations. The engine speed and torque are supplied by the vehicle's ECU.

As indicated above, the vehicle monitor collects data used to measure the durability and efficiency of the components available for use in building a vehicle. Using measures of duty as described above, and knowledge of vehicle component wear state or failure state or efficiency, the vehicle monitor forms estimates of each component of interest's durability or efficiency under known, measured usage. This data is then used to form a model of each component of interest's durability under three different failure or wear out mechanisms: cyclic fatigue failure, ultimate strength (bending) failure, and frictional or tribological wear. Depending on the component, most component failure or wear-out can be usefully described by one of these three patterns. The data is also used to form a model of each component's efficiency under all operating conditions.

Cyclic fatigue failure occurs when a component has been under repeated cycles of stress less than the stress to produce permanent bending. As the number of cycles increases, the part will eventually fail, especially at higher stress levels. This phenomenon is shown graphically in an S—N curve that depicts the number of cycles possible at a given stress level before a failure occurs.

Cyclic fatigue failures commonly occur in suspension components after many miles of driving on rough roads, which create large repeated stresses on the components.

Overall suspension cyclic loading can be measured using a number of different sensors: a chassis-mounted accelerometer to calculate overall suspension-driven forces on the chassis, an air-suspension height measurement to show suspension displacements driven by road roughness, air-suspension pressure measurements to help estimate suspension static loading, wheel angular displacement sensors (ABS sensor, toothed wheel and magnetic sensor) to show instantaneous wheel accelerations due to road roughness.

Ultimate strength failures occur when a component is stressed to the point that it bends permanently. These failures commonly occur when a component is overloaded or operating at normal load levels in an overheated state. Ultimate strength failures commonly occur when components are subject overloads such as hitting a pothole in the road. For suspension components, the sensors may be the same as those measuring cyclic fatigue (above).

Frictional or tribological wear is related to components in sliding or rolling contact. The amount of wear is related to the force of contact, lubrication state of the contact, temperature of the contact and time of the contact.

By measuring these parameters, the vehicle monitor can form an estimate of frictional wear or tribological wear. Frictional or tribological wear commonly occurs in brakes and clutches (frictional wear) or bearings and gears (tribological wear). In these cases, the amount of energy dissipated or transmitted by the component is an indicator or wear. Sensors for measuring energy dissipated in a system are described above in the brake duty and clutch duty descriptions. Engine energy production is measured using ECU-supplied torque, power and engine speed.

The vehicle monitor may estimate the engine efficiency in a particular application.

The vehicle monitor may measure the engine's Brake-Specific Fuel Consumption (BSFC) at every engine speed and engine torque level in the engine's operating range. The vehicle monitor may observe the engine's fuel consumption as supplied by the ECU, the engine's torque level as supplied by the ECU and the engine's speed as supplied by the ECU.

Figure 4:
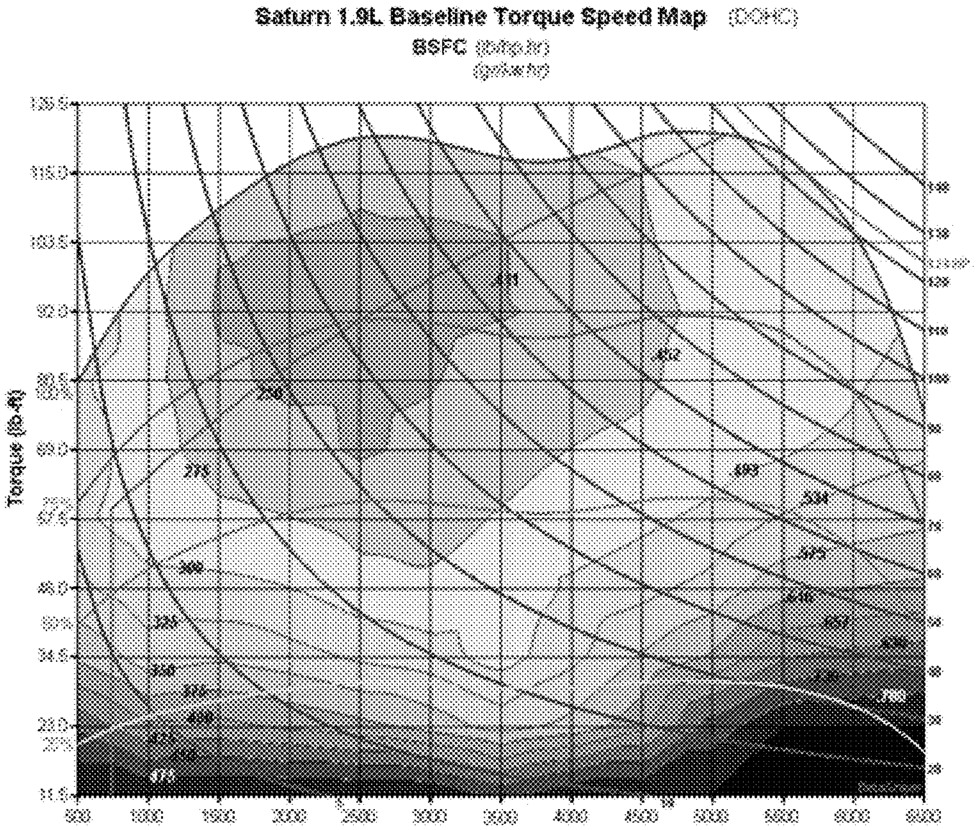
FIG. 4 illustrates a graph.

This data is stored in a two-dimensional map as shown in FIG. 4.

The x-axis shows engine speed. The y-axis shows engine torque. The coloring and contour lines show the brake power specific fuel consumption (grams/hour per kilowatt of power (g/kw·hr). This map when combined with the actual duty of the vehicle can estimate the vehicle's fuel consumption for the specified duty.

This is done by using the time-at-speed-and-torque map described above to determine time and then determining the fuel consumption rate at each torque and speed point by lookup in the BSFC map.

Then, by multiplying time by fuel consumption rate, the vehicle monitor may get total fuel consumed at every speed and torque point (time (hr)*fuel rate (gr/hr)). The vehicle monitor may then add up the fuel consumed at each speed and torque point to determine the total fuel consumed for the given duty.

Overall vehicle performance can also be estimated with MTBF, repair rates and other measures given a known duty cycle.

For components that are subject to cyclic fatigue failure an S—N curve is formed from field data of failed components. The S—N curves of many similar failed components are averaged together to form a cyclic fatigue model for that component. The S—N curve is then used with a linear theory of accumulated damage (Miner's Rule) to estimate the durability of the component given the measured duty cycle.

For components that are subject to ultimate strength failure (bending or overloading, described above) field data is used to determine the maximum loading that a given component is subjected to. For example, to evaluate suspension-loading, vehicle mounted accelerometers can measure vertical accelerations of the vehicle related to rough roads or roads with uneven surfaces. The vehicle's axle and suspension system transmits forces from the roadway surface to the mass of the vehicle.

The magnitude of the vertical accelerations is proportional to the forces needed to create the accelerations (F=ma). Forces to create the vertical accelerations of the vehicle are added to forces needed to support the weight of the vehicle (mass of vehicle times acceleration of gravity) to form a suspension loading profile. The peak forces transmitted by the axle and suspension system can then be determined by the peak accelerations observed in the field data.

For components that are subjected to frictional wear or tribological wear, a measure of the total energy dissipated in the system (brakes and clutches) or transmitted by the system (gears and bearings) along with known, measured wear is used to form an energy-based wear-out measure. For example, using the accumulated brake energy measure mentioned above made on worn out brake components indicates the energy the brakes are capable of dissipating before wear out.

The remote computer and/or the vehicle computer may analyze data from the following sources:

a. OEM system and sub-system durability data or usable life estimates generated by engineering analysis and laboratory testing.

b. Vehicle monitor vendor supplied, field empirical, system and sub-system durability data or usable life estimates generated by comparing wear-out and repair history to vehicle duty (as described above), c. A list of plausible vehicle configurations or vehicle configurations acceptable to the customer.

The above are used produce a vehicle system performance model and test each particular configuration for performance against goals.

The vehicle system performance model that describes a component wear-out, component failure, system efficiency or other parameter of interest is run with the measured duty of the application to produce ratings of the different configurations.

For example: the measured duty is used with an S—N based fatigue model and the theory of accumulated damage to estimate the durability of components of interest in each vehicle configuration. These durability estimates are compared to OEM and customer needs (e.g. projected warranty cost, projected down time, projected fuel efficiency, etc.) to determine which configurations meet OEM application durability needs and customer cost targets.

The theory of accumulated damage uses an S—N curve to estimate the number of cycles possible at any given level of stress. When a component is subject to a given level of stress, for which N cycles are possible, the vehicle monitor may say that 1/N of the life of the component is used up. If the vehicle monitor may keep track of each stress cycle the component undergoes, the vehicle monitor can tally up how much component life is used in each cycle. At some point in the component's life, the tally will indicate that all of the component's life is used up. At this point, the vehicle monitor may recommend replacing or overhauling the component.

When the number of plausible vehicle configurations is large enough that computing ratings for each configuration is not possible a goal seeking and optimization of configurations is accomplished in any of a number of different ways:

a. Manual modification of configurations, where the user is in the loop changing configurations to seek better results, b. Automated modification of configurations using Monte Carlo, partial derivative optimization or other techniques to seek better results.

c. Massive parallel analysis of all possible configurations and subsequent sorting/searching for optimal configurations.

Figure 5:
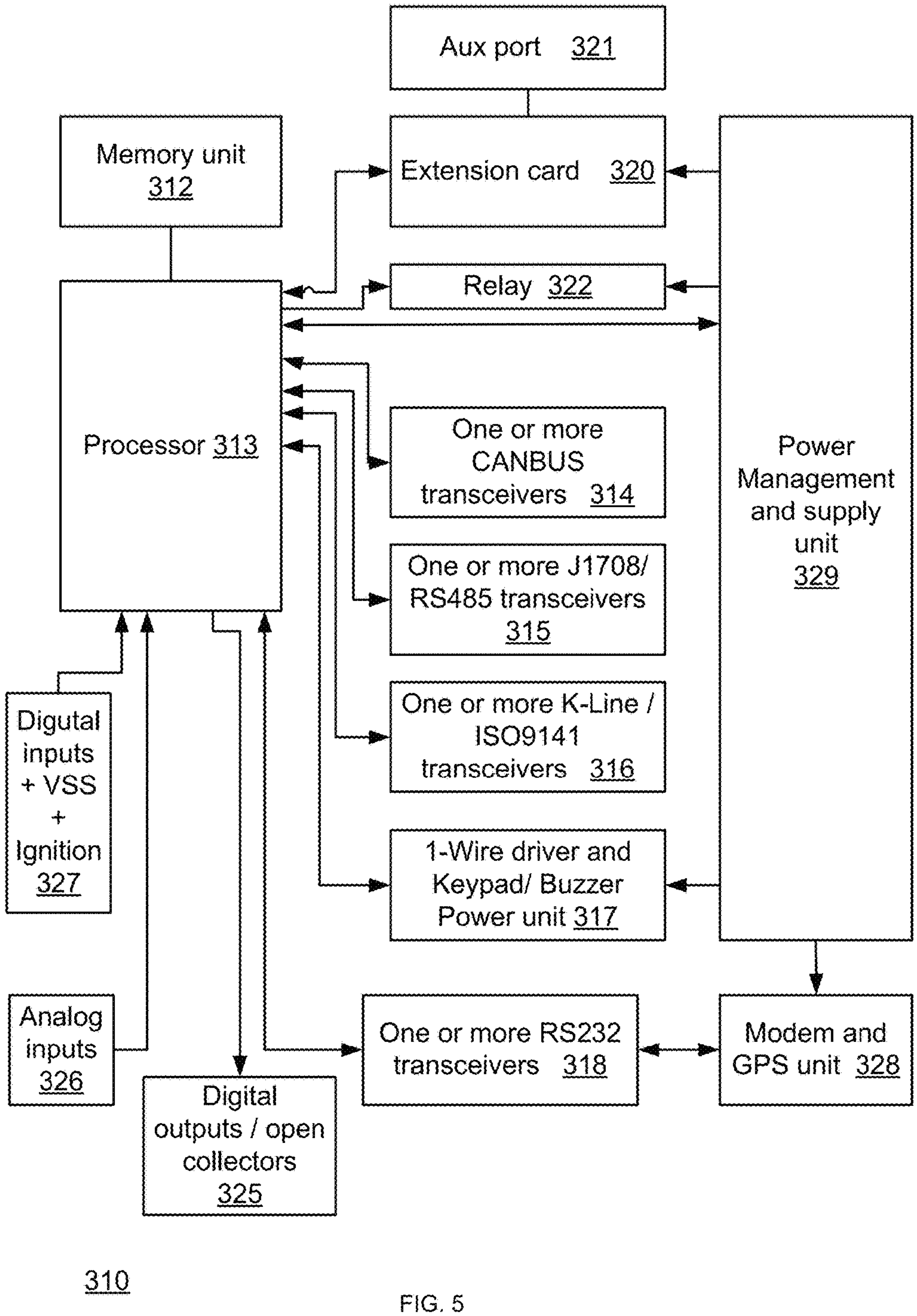
FIG. 5 illustrates a vehicle monitor according to an embodiment of the invention.

FIG. 5 illustrates an example of a vehicle monitor 310.

Vehicle monitor 310 includes processor 313, memory unit 312, power management and supply unit 329, modem and GPS unit 328 and various input output units such as one or more CANBUS transceivers 314, one or more J1708/RS485 transceivers 315, one or more K-Line/ISO9141 transceivers 316, one or more RS232 transceivers 318, 1-wire driver and keypad/buzzer power unit 317, digital inputs and VSS+ ignition unit 327, analog inputs 326, digital outputs/open collectors 325, extension card 320 and aux port 321.

The various input output units are merely examples of various types of connections/links between the processor 313 to other units (such as sensors 340, 342 and 344 of FIG. 3 and/or controllers 330 of FIG. 3).

Memory unit 312 may be a non-volatile memory unit and/or a combination of volatile and non-volatile memory units.

The vehicle monitor 310 may include multiple processors—especially when the vehicle monitor 310 is configured to calculate the performances of the vehicle.

Figure 6:
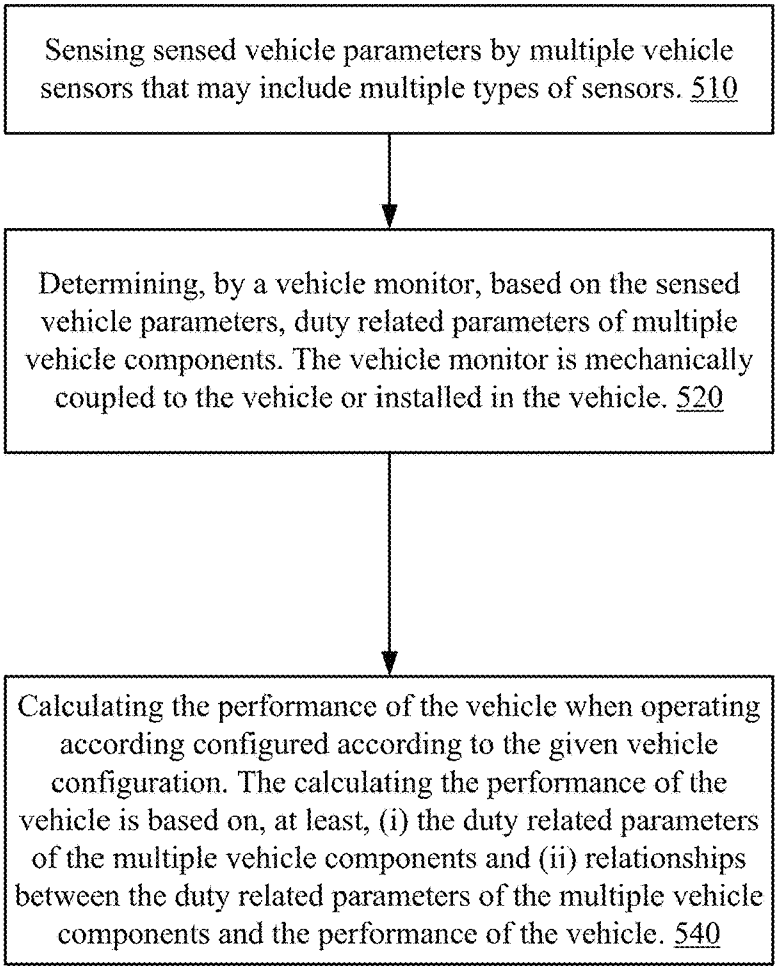
FIG. 6 illustrates a method according to an embodiment of the invention.

FIG. 6 illustrates method 500 according to an embodiment of the invention.

Method 500 is for evaluating a performance of a vehicle when the vehicle is operated according to a given application.

Method 500 may start by step 510 of sensing sensed vehicle parameters by multiple vehicle sensors that may include multiple types of sensors. The sensors may be read by multiple means, as analog voltages, digital values or network data packets. The sensors include those commonly fitted to the vehicle such as, a measure of time, engine oil pressure, coolant temperature, wheel angular rotating displacement and tire pressure.

Step 510 may be followed by step 520 of determining, by a vehicle monitor, based on the sensed vehicle parameters, duty related parameters of multiple vehicle components. The vehicle monitor is mechanically coupled to the vehicle or installed in the vehicle. For example, the amount of time the vehicle is operated on rough roads and the magnitude of that road roughness determine the duty of many different components on the vehicle including tires, axles, suspension linkages, suspension bushings and suspension springs.

Step 520 may include at least one of the following:

a. Determining a stress cycle histogram of a vehicle component.

b. Estimating an energy dissipated by one or more vehicle components.

c. Estimating an energy dissipated by a vehicle brake during a braking process by multiplying a calculated or measured mass of the vehicle by a sum of (i) a change of vehicle speed during the breaking process and (ii) a change of vehicle altitude during the breaking process.

d. Measuring a distribution of engine power over time.

e. Measuring a distribution of transmission transmitted power over time.

f. Measuring a distribution of power dissipated by the clutch over time.

g. Adding a static force applied on a suspension of the vehicle to estimated dynamic forces applied on the suspension during movement of the vehicle.

Step 520 may be followed by step 540 of calculating the performance of the vehicle when operating according to the given vehicle configuration.

Step 540 may include calculating the performance of the vehicle based on, at least, (i) the duty related parameters of the multiple vehicle components and (ii) relationships between the duty related parameters of the multiple vehicle components and the performance of the vehicle. For example, vehicle fuel consumption for a particular vehicle configuration and driving duty is calculated by combining the engine's measured brake specific fuel consumption, the driveline's (transmission and axle) gear ratio configurations and the measured duty of the vehicle.

Step 540 may include at least one of the following:

a. Calculating performance parameters of the multiple vehicle components. For example—calculating the durability and/or efficiency of multiple vehicle components.

b. Calculating the performance of the vehicle based on the performance parameters of the multiple vehicle components.

c. Calculating a durability of each of the multiple vehicle components.

d. Calculating a durability of at least one vehicle component based on a cyclic fatigue failure of the at least one vehicle component.

e. Calculating a durability of at least one vehicle component based on an ultimate strength failure of the at least one vehicle component.

f. Calculating a durability of at least one vehicle component based on frictional wear or tribological wear of the at least one vehicle component.

g. Calculating performance parameters of the vehicle systems.

Steps 510, 520 and 540 may be applied while the vehicle is configured according to a certain configuration and step 540 may reflect the performance of the vehicle if of the given configuration and when the vehicle is operated according to a given application.

There may be a need to evaluate the performance of the vehicle when the vehicle is operated according to the given application but is configured in multiple configurations.

Duty related parameters of the multiple vehicle components (when the vehicle is configured to another configuration) may be measured on another vehicle, may be measured by the vehicle during a period in which the vehicle was configured according to other configuration and was operated according to the given application.

Additionally or alternatively, duty related parameters may be deducted based on information provided by the OEM, by clients of the OEM, by and the like.

Accordingly—step 540 can be executed multiple times—once per each configuration of the multiple applications.

After the evaluation of the vehicle performance at different vehicle configurations (and according to the application of interest) the method may select a selected vehicle configuration. The selected vehicle configuration can be, for example, the cheapest vehicle configuration that can withstand the application of interest. Any other selection parameter may be used.

Figure 7:
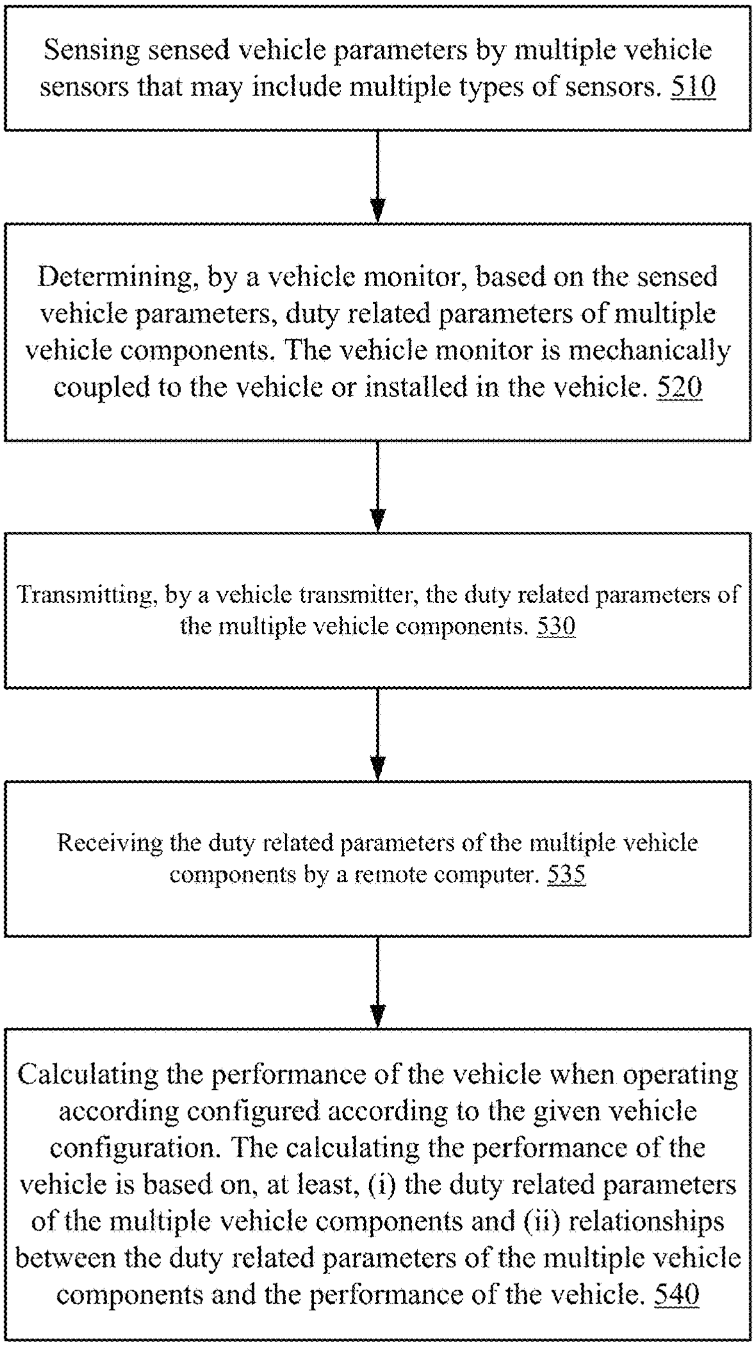
FIG. 7 illustrates a method according to an embodiment of the invention.

FIG. 7 illustrates method 502 according to an embodiment of the invention.

Method 502 is for evaluating a performance of a vehicle when the vehicle is operated according to a given application.

Method 502 may start by step 510 of sensing sensed vehicle parameters by multiple vehicle sensors that may include multiple types of sensors.

Step 510 may be followed by step 520 of determining, by a vehicle monitor, based on the sensed vehicle parameters, duty related parameters of multiple vehicle components. The vehicle monitor is mechanically coupled to the vehicle or installed in the vehicle.

Step 520 may be followed by step 530 of transmitting, by a vehicle transmitter, the duty related parameters of the multiple vehicle components.

The vehicle transmitter may be included in the vehicle monitor, may be coupled to the vehicle monitor, may be included in a communication unit, and the like.

The aggregate size of the duty related parameters of the multiple vehicle components may be less than one thousandth of an aggregate size of the sensed vehicle parameters.

The aggregate size of the duty related parameters of the multiple vehicle components is a fraction (for example less than $1/100$ or $1/1000$ or $1/10000$ of $1/1,000,000$) of the aggregate size of the sensed vehicle parameters.

Step 530 may be followed by step 535 of receiving the duty related parameters of the multiple vehicle components by a remote computer.

Step 535 may be followed by step 540 of calculating the performance of the vehicle when operating according configured according to the given vehicle configuration.

Step 540 may be executed by the remote computer.

There may be a need to evaluate the performance of the vehicle when the vehicle is operated according to the given application but is configured in multiple configurations.

Duty related parameters of the multiple vehicle components (when the vehicle is configured to another configuration) may be measured on another vehicle, may be measured by the vehicle during a period in which the vehicle was configured according to other configuration and was operated according to the given application.

Additionally or alternatively, duty related parameters may be deducted based on information provided by the OEM, by clients of the OEM, by and the like.

Accordingly—step 540 can be executed multiple times—once per each configuration of the multiple applications.

After the evaluation of the vehicle performance at different vehicle configurations (and according to the application of interest) the method may select a selected vehicle configuration. The selected vehicle configuration can be, for example, the cheapest vehicle configuration that can withstand the application of interest. Any other selection parameter may be used.

Figure 8:
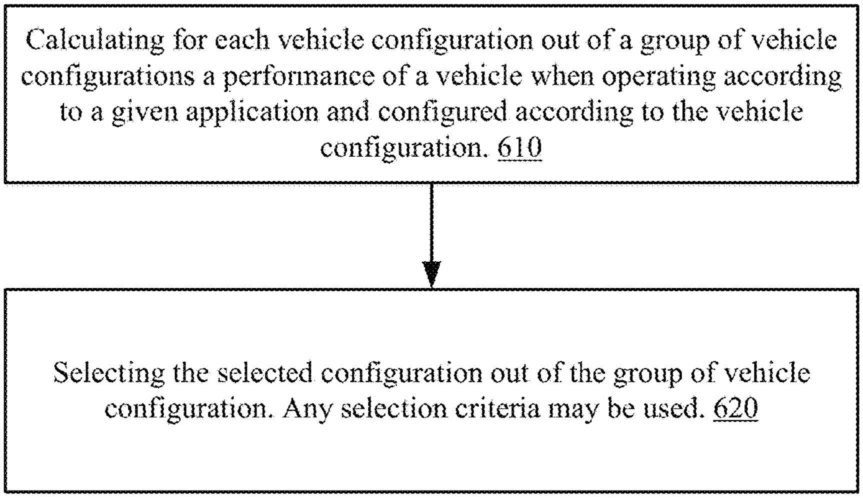
FIG. 8 illustrates a method according to an embodiment of the invention.

FIG. 8 illustrates method 600 according to an embodiment of the invention.

Method 600 may be used for selecting a selected vehicle configuration.

Method 600 may start by step 610 of calculating for each vehicle configuration out of a group of vehicle configurations a performance of a vehicle when operating according to a given application and configured according to the vehicle configuration.

Step 610 may be followed by step 620 of selecting the selected configuration out of the group of vehicle configuration. Any selection criteria may be used.

Step 610 may include executing steps 510, 520, 530 and 540.

Duty related parameters of the multiple vehicle components (when the vehicle is configured to another configuration) may be measured on another vehicle, may be measured by the vehicle during a period in which the vehicle was configured according to other configuration and was operated according to the given application.

Additionally or alternatively, duty related parameters may be deducted based on information provided by the OEM, by clients of the OEM, by and the like.

Any one of method 500, 502 and 600 may include determining, by the vehicle monitor, based on the sensed vehicle parameters, efficiency related parameters of at least one vehicle components. This may be executed in addition to or instead of step 520.

Figure 9:
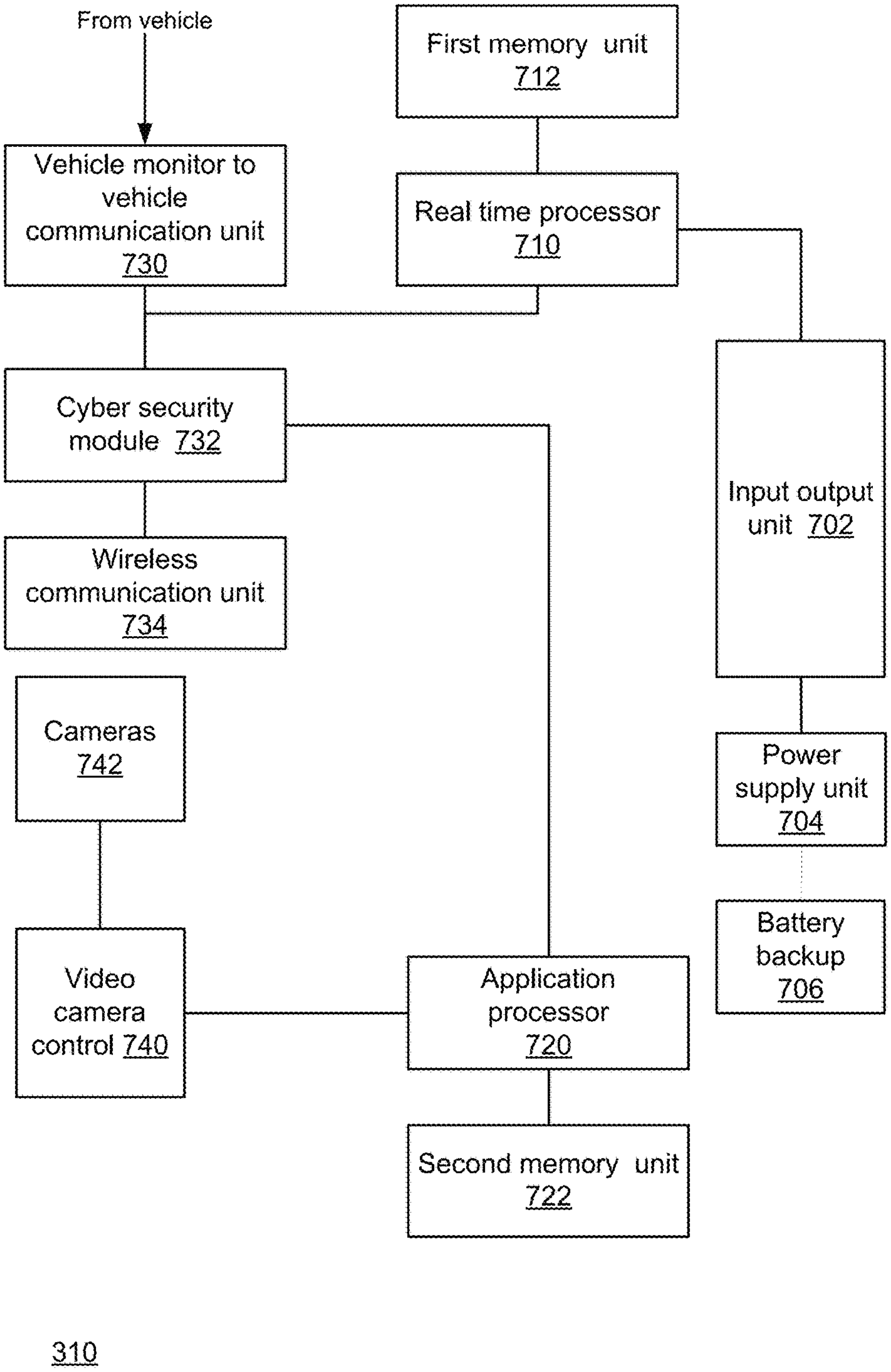
FIG. 9 illustrates a vehicle monitor according to an embodiment of the invention.

FIG. 9 illustrates vehicle monitor 700 according to an embodiment of the invention.

Vehicle monitor 700 include a real-time processor 710, an application processor 720, first memory unit 712, second memory unit 722, cyber security module 732, multiple communication units/interfacing units such as vehicle monitor to vehicle communication unit 730, wireless communication unit 734 and input output unit 702.

The vehicle monitor 700 may include and/or may be coupled to sensors such as video cameras 742, accelerators and the like.

The input output unit 702 may be coupled to various sensors via buses such as analog buses, digital buses, may be coupled to relays, and the like. Non-limiting examples of various communication protocols that are supported by the input output unit 702 and/or buses may include RS232, RE485, J1708, CANBUS, K-line, HAMI, VGS, IBIS and AV and/or DC feeds.

The wireless communication unit 734 may wirelessly communicate using any wireless protocols such as but not limited to Wi-Fi, Bluetooth, BLE, 3G cellular, 4G cellular, 433 Mhz RF link, LORA.

Vehicle monitor to vehicle communication unit 730 interfaces between the vehicle monitor and vehicle systems, vehicle sensors vehicle system controllers and the like. Non-limiting protocols and/or buses supported include CANBUS, OBD, J1708 and LIN.

Cyber security module 732 mitigates cyber attacks and may be coupled between the wireless communication unit 734, the real-time processor 710, the application processor 720 and the vehicle monitor to vehicle communication unit 730.

The real-time processor 710 and the application processor 720 can be any hardware processors such as but not limited to CORTEX-A7 and CORTEX-M4 of Qualcomm Inc.

The first memory unit 712 is coupled to real time processor 710. Second memory unit 722 is coupled to application processor 720.

Real-time processor 710 may process data from sensors in real time while application processor 720 may execute more complex tasks (that may be less urgent) such as determining an actual wear of a vehicle, and the like.

Faster Product Improvement

In heavy trucks, warranty failures and diagnostic trouble codes (DTCs) drive most of today's product improvement efforts.

OEMs current processes are driven by field failure rates and onboard Diagnostic Trouble Codes (DTCs). The OEMs current product improvement method is driven by feedback from the field after failures occur.

In an improvement method with feedback driven by failures, truck users always suffer the inconvenience and economic loss associated with field failures before problems are fixed. In the new improvement method, feedback on component and system performance is obtained and analyzed in advance of failures. This feedback is based on detailed observation of component performance and analysis of component performance performed on a monitor system in the vehicle. By performing the analysis in the vehicle, we avoid the cost of moving large amounts of data from observations across a wireless network. Only the high-level summaries of component performance are moved across the network. This system has the further advantage of offering immediate, real-time alerts to the driver should a component be near failure because time to transport data across the network is eliminated.

There is provided a system, method and computer readable medium that stores instructions that cost effectively observes system performance in all or most of a large production run of trucks and predicts failures and DTCs long before they happen. Truck OEMs can then initiate product improvement actions before failures occur.

The method works by making accurate online measurements of truck systems' performance and then using these measurements to learn system performance trends.

The combination (e.g. average) of trends from many similar trucks over time form a background that illustrates the normal performance of the truck in field use. For a particular truck, at particular time, when the observed trend varies significantly from background or expected trends or otherwise indicates an impending failure, the system sends a notification for further investigation.

Expected, normal operating range, performance trends are generated from Statistical Process Control (SPC) type techniques based on engineering models from both analytic (engineering equations) and empirical sources (on-the-road data gathered by a telematics system). This technique involves observing a particular parameter of interest (e.g. coolant temperature, engine Brake Specific Fuel Consumption) and using statistical correlations to explain variation of the parameter using other parameters related to the truck or its operating condition (e.g. ambient air temperature, truck speed, truck mass). Next create a model of the observed parameter of interest with the effects of other parameters removed. This model is then used with data from many trucks in normal operation to determine the amount of unexplained variation in the model.

For example, a model describing engine coolant temperature accounts for a number of factors that change the coolant temperature during operation. These factors include ambient air temperature, engine rpms, engine power, vehicle speed and radiator fan speed (if driven separately from the engine speed). The model is formed using field observations of the coolant temperature and the other factors mentioned above measured at the same time. For a normally operating truck, we use a multiple linear regression model to estimate the influence of each factor (input variables) on the coolant temperature (response variable). We then calculate the standard deviation of the model's output of coolant temperature with respect to the measured field data. The standard deviation describes the amount of unexplained variation in the model.

For trucks in operation, we will often set the allowable difference between model output and measured coolant temperature at 2 times the standard deviation of the model. This means that, for normally distributed model errors, the measured value is within the threshold 95% of the time.

The model output and the amount of unexplained variation in the model output for normal truck operation form the basis of comparison to trucks operating in the field (this is the normal operating range of the parameter). For a truck in the field, when the model of the observed parameter of interest exceeds the normal unexplained variation level, the truck is flagged for further investigation as to why the modeled parameter exceeded normal unexplained variation. This reason is often a system or component performance degradation or failure.

In some cases, the duty a system is subjected to influences the performance of the system.

In these cases, the duty cycle is measured and used as an input to the system performance trend analysis. For example, trucks subjected to heavy loading will wear out at a higher rate than trucks subjected to light loads. The loading duty cycle will be an important factor in determining the variation in many truck parameters.

The online measurement of the truck systems performance may involve direct measurements of easily interpreted parameters and may also include performance measures based on combinations of measured parameters used to infer system performance.

Online access and a help-desk type facility gives users responsible for product improvement access to automatically generated flags and underlying data. For example, an online control chart of the parameter of interest displayed with other vehicle operating parameters.

In some cases, the diagnostic system and/or the electronic controls of the truck system under observation may be reprogrammed while in use (OTA—Over the Air reprogramming). This is done with a secure wireless download capability. In use reprogramming, may help the diagnostic system home in on a problem or may help resolve a field issue. For example, because components can fail in many different ways and that it is not possible to fit computer code for every type of failure in a mobile computing platform we provide for dynamically loadable analysis code packages. When the overall system monitor detects that particular component is trending away from normal operation, we send an analysis code package to the in-vehicle monitor that specifically targets analyzing data for the component in question. The goal of this operation is not just to identify that the component is trending away from normal operation, but also to make a more detailed analysis to determine why (root-cause) the component is trending this way.

Figure 10:
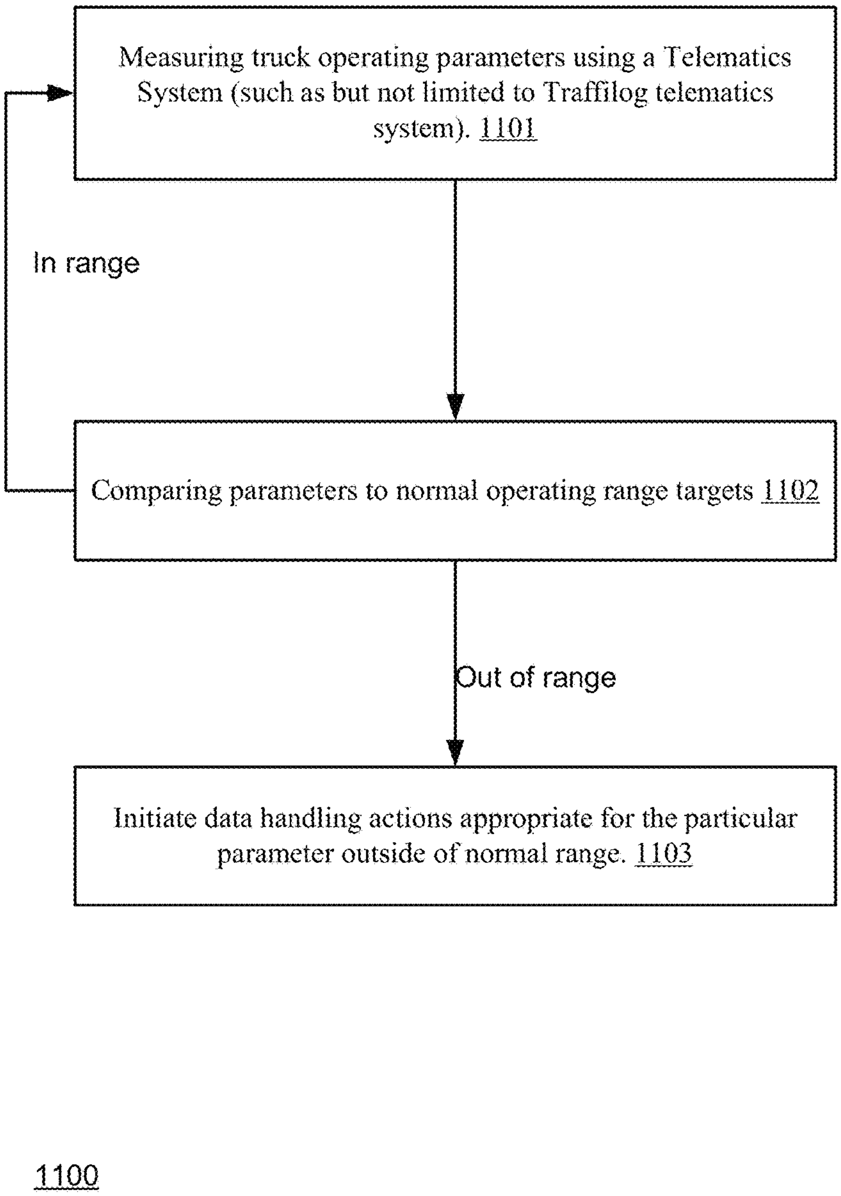
FIG. 10 illustrates a method according to an embodiment of the invention.

FIG. 10 illustrates method 1100 according to an embodiment of the invention.

Method 1100 may start by step 1101 of measuring truck operating parameters using a vehicle monitor (such as a telematics system—such as but not limited to Traffilog Multi-Bus Unit telematics system).

The parameters may include, for example:

a. Measured values (e.g. vehicle speed, engine coolant temperature, pressures, etc.), b. Filtered values—measured values averaged or filtered over a period of time, c. Calculated values—mathematical combinations of other values (e.g. speed is a combination of distance traveled divided by the time to travel that distance, engine efficiency is a combination of measured engine power output and measured engine fuel consumption), d. Inferred values—values created by inferring the internal state of a system using the above values and a system model (e.g. brake remaining useful life is a combination of all brake usage information and a brake wear-out model).

Step 1101 may be followed by step 1102 of comparing parameters to normal operating range targets.

Normal operating range targets may be set, for example, using one or more of the following techniques:

a. Simple thresholds—operating range target that does not change over time.

b. Dynamic thresholds—operating range target that changes as a function of time or as a function of another parameter (e.g. engine load, total brake energy dissipated, etc.).

c. Configuration specific thresholds—operating range targets that are influenced by the truck's particular configuration (e.g. engine size, transmission ratios).

d. Calculated thresholds—operating range targets that are a function of a system model or other calculation (e.g. brake remaining useful life, catalyst temperature).

e. Population specific thresholds—operating range targets that are a function of a population's observed performance (e.g. mean plus or minus 1 standard deviation to set threshold).

f. Rate specific thresholds—thresholds set in part by the rate at which the parameter of interest is changing (related to a threshold for the derivative of the parameter of interest) (e.g. thresholds for exhaust gas temperature normal variability get wider when rate of change of engine speed is large).

g. Integrated specific threshold—thresholds set in part by the accumulated value of the parameter over some period of time (related to the integral of the parameter of interest) (e.g. thresholds for coolant temperature normal variability get wider when cooling system operating hours increases, change due to lower radiator capability with dirt and wear, lower coolant pump capability with pump and drive belt wear).

Normal operating range is expected to be between the upper threshold and lower threshold of the parameter. For example, if normal engine operating temperature is 90 C the threshold may be +/−5 C for a new truck and +/−7 C for a used truck.

If the parameters are within normal operating range, then step 1102 is followed by step 1101.

If the parameters are outside of normal operating range jumping to step 1103.

Step 1103 may include initiate data handling actions appropriate for the particular parameter outside of normal range.

Step 1103 may include, for example:

a. Sending a notification of the out of range parameter.

b. Sending a snapshot of the conditions before, during or after the out of range circumstance.

c. Initiating specialized data collection, data analysis or data transmission to collect detailed information around the circumstances of the out of range condition.

Step 1103 may be followed by step 1101.

As a result of notifications listed above initiate system improvement actions necessary to avoid field failures and warranty costs.

Method 1100 may be executed by a computer or by a system that includes a computer as well as information sources and/or sensors such as vehicle monitors.

Figure 11:
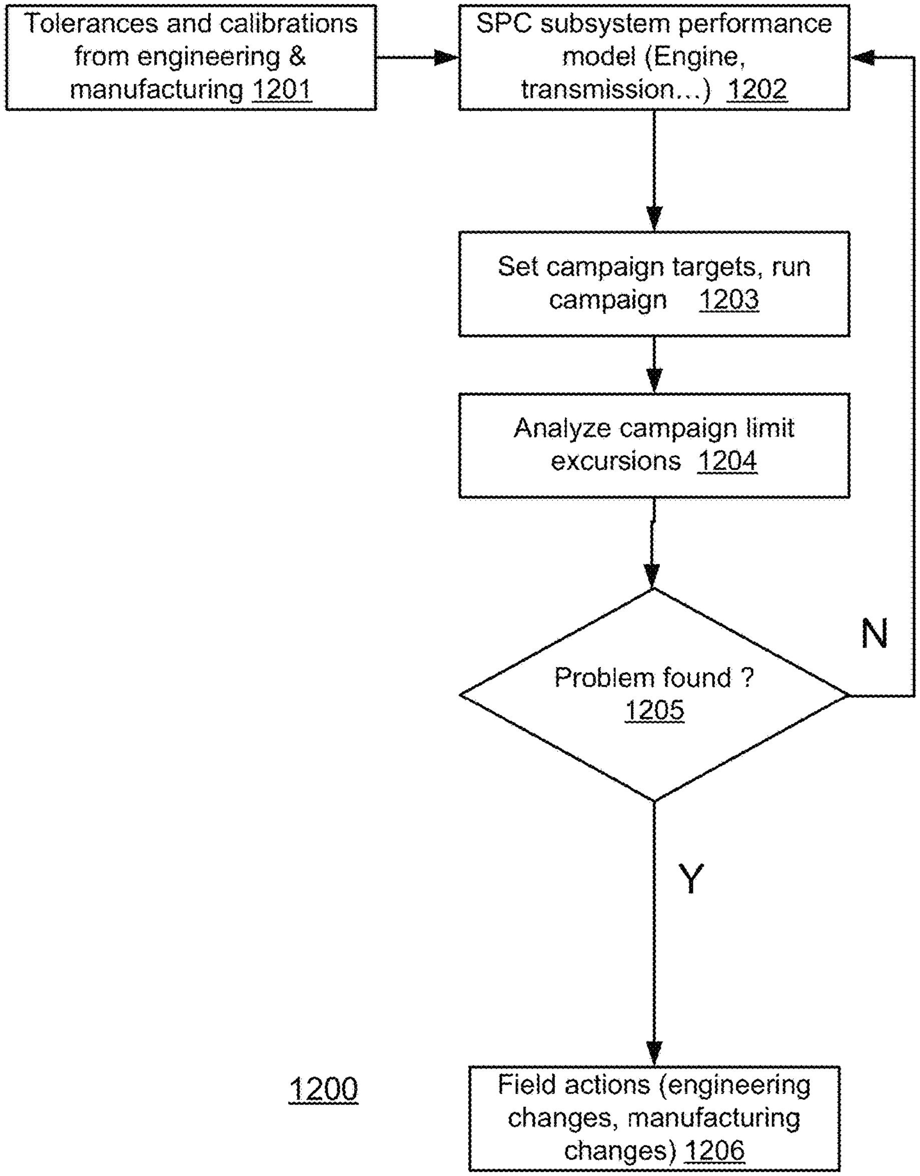
FIG. 11 illustrates a method according to an embodiment of the invention.

FIG. 11 illustrates method 1200 that includes steps 1201 through 1206—that are one particular example of the process described by steps 1101 through 1103.

Step 1201 creates tolerances and calibrations for an online observation process. The tolerances set the allowable range of observed operation before signaling a fault. The calibrations are used by algorithms in the observer that can modify the tolerances depending on conditions in the vehicle. For example, the battery voltage during engine cranking is a function of battery state of charge, number of charge/discharge cycles on the battery, starter current draw, and battery temperature. In a typical battery model, each of these terms have a factor that relates the parameter to battery voltage during cranking. Battery Voltage during crank=Base voltage+a*state of charge+b*number of cycles+c*starter current+d*battery temperature, where a, b, c, d are factors for parameters state of charge, number of cycles, starter current, battery temperature respectively. This calibrated voltage is then the expected value of the voltage measured on the truck plus or minus the supplied tolerance.

Step 1202 uses the calibrations to calculate and apply changes to tolerances during testing. This allows the system to track changes in the vehicle's operating condition and relate this to expected changes in measured parameters.

Step 1203 is an observation process that reads measurements of the system under test and compares those measurements to current tolerances.

Step 1204 analyzes measurements that are outside of the current tolerances (called limit excursions) to determine if a problem is found. For example, a single out of tolerance value of a particular measurement may not indicate a problem. By contrast, a series of out of tolerance values of a particular measurement may indicate a problem.

Step 1205 branches to 1206 if a problem is found or branches to 1202 if no problem is found.

Step 1206 notifies responsible parties that a problem was found. The responsible parties would then initiate changes to the product or test system to address the problem. The product may be modified in the field by Over the Air (OTA) reprogramming of electronic control modules. The test system may be modified in the field by OTA reprogramming of the software in the field test system.

Methods 1100 and/or 1200 may be executed by a computer, a vehicle monitor, and the like.

Figure 12:
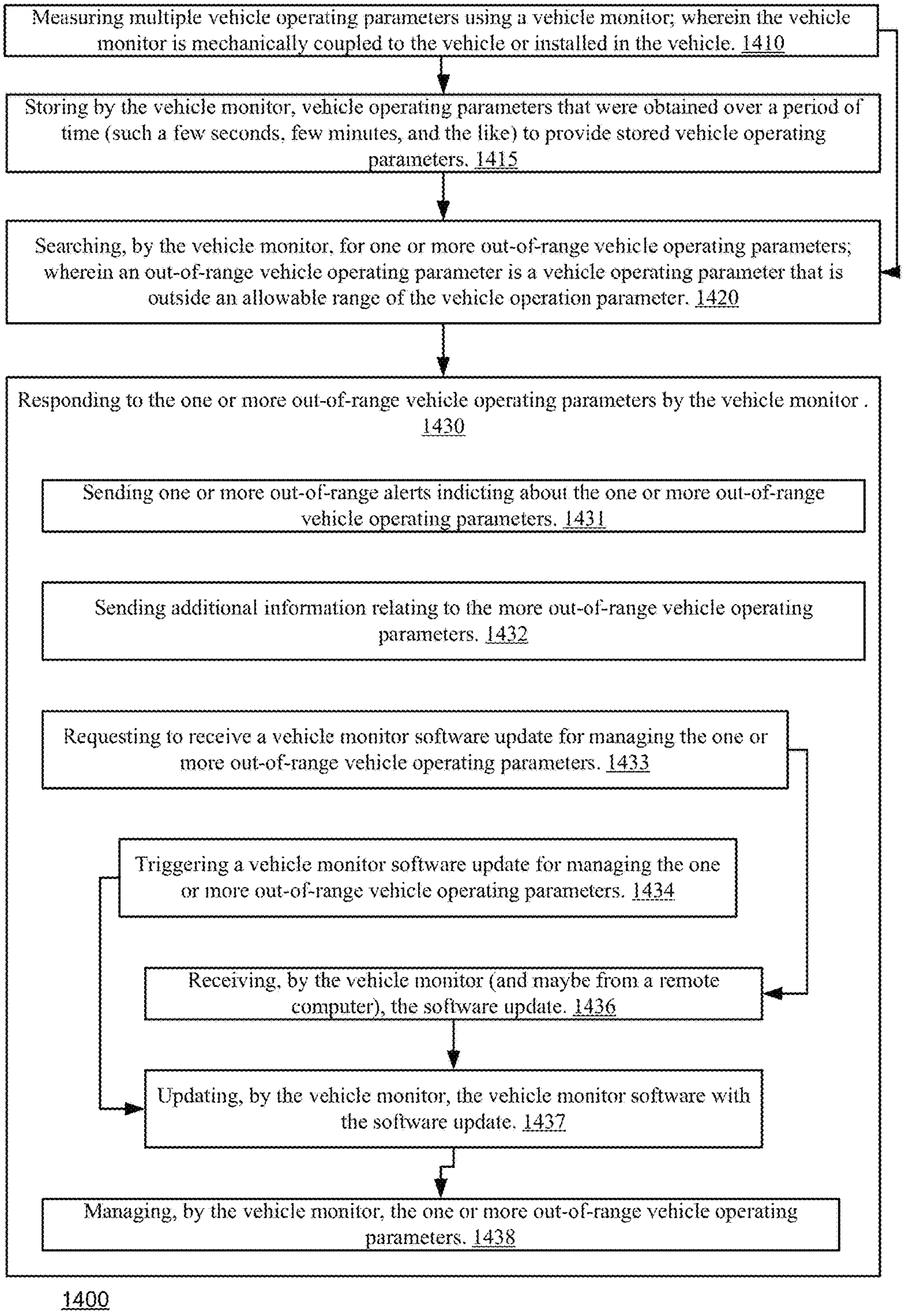
FIG. 12 illustrates a method according to an embodiment of the invention.

FIG. 12 illustrates method 1400 according to an embodiment of the invention.

Method 1400 may start by step 1410 of measuring multiple vehicle operating parameters using a vehicle monitor; wherein the vehicle monitor is mechanically coupled to the vehicle or installed in the vehicle.

Examples of measuring vehicle parameters are provided in the section above titled "ACCURATE APPLICATION APPROVAL".

Step 1410 may be followed by step 1415 of storing by the vehicle monitor, vehicle operating parameters that were obtained over a period of time (such a few seconds, few minutes, and the like) to provide stored vehicle operating parameters.

Step 1410 may be followed by step 1420 of searching, by the vehicle monitor, for one or more out-of-range vehicle operating parameters; wherein an out-of-range vehicle operating parameter is a vehicle operating parameter that is outside an allowable range of the vehicle operation parameter.

The allowable range of a vehicle operation parameter may be fixed, dynamic (change over time and/or based on an event), may be time dependent, may be dependent upon a value of one or more other vehicle operation parameters, may depend on the configuration of the vehicle, may depend on a rate of change of a value of the vehicle operation parameter and/or may depend upon an accumulated value of the vehicle operation parameter over a period of time.

If not finding any out-of-range vehicle operating parameter, then jumping to step 1410.

When finding out-of-range vehicle operating parameters then jumping to step 1430 of responding to the one or more out-of-range vehicle operating parameters by the vehicle monitor.

The one or more out-of-range vehicle parameters may be indicative of at least one vehicle failure that is impending (still did not occur).

Step 1430 may precede the occurrence of the at least one vehicle failure.

Step 1430 may include at least one of the following:

a. Sending one or more out-of-range alerts indicting about the one or more out-of-range vehicle operating parameters. (Step 1431).

b. Sending additional information relating to the more out-of-range vehicle operating parameters. (Step 1432).

c. Requesting to receive a vehicle monitor software update for managing the one or more out-of-range vehicle operating parameters. (Step 1433).

d. Triggering a vehicle monitor software update for managing the one or more out-of-range vehicle operating parameters. (Step 1434).

Step 1431 may include sending the one or more out-of-range alerts to a system that is external to the vehicle, and/or sending the one or more out-of-range alerts to a vehicle system and/or generating one or more human perceived out-of-range alerts.

When an out-of-range parameter is detected, the monitoring system operation may be modified to collect more detailed information related to the out-of-range parameter. The operation is modified by updating monitoring software in real-time, during vehicle operation. The change in monitoring system operation may be as simple as collecting and transmitting more raw data from the out-of-range system or as complex as calculating more system state parameters from all sources of data on the vehicle. For example, when the engine coolant temperature goes out-of-range, we may capture more detailed information on the engine's operating power, torque and speed and use this with a thermal efficiency model of the engine to determine cooling system load during the time of out-of-range temperatures.

Referring to step 1432—the additional information may include a plurality of the stored vehicle operating parameters, and/or a snapshot of the at least some of the multiple vehicle operating parameters before finding the one or more out-of-range vehicle operating parameters, and/or a snapshot of the at least some of the multiple vehicle operating parameters after finding the one or more out-of-range vehicle operating parameters.

Step 1433 may be followed by step 1436 of receiving, by the vehicle monitor (and maybe from a remote computer), the software update.

Step 1436 and 1434 may be followed by step 1437 of updating, by the vehicle monitor, the vehicle monitor software with the software update.

Step 1437 may be followed by step 1848 of managing, by the vehicle monitor, the one or more out-of-range vehicle operating parameters.

Step 1848 may include at least one out of changing a configuration of a vehicle component associated with the one or more out-of-range vehicle operating parameters and changing a monitoring parameter associated with the one or more out-of-range vehicle operating parameters. The monitoring parameter may include a frequency of monitoring, the resolution of monitoring, the duration in which monitoring result are stored at the vehicle monitor and the like.

Faster New Feature Launch

Regulations for safety, fuel-efficiency and greenhouse gasses are changing at an accelerating rate. Truck OEMs respond to new regulations with new products that are more complex and need to be launched on compressed schedules. Historically, all new product feature launches include extensive laboratory testing and extensive field-testing. This invention shortens the amount of time and reduces the cost to complete this testing.

In many cases, the OEMs initial laboratory testing and field-testing is not adequate to insure a successful launch. This system helps by allowing field-testing of a larger population and by spotting problems before they become failures. Also, the system can accurately measure and characterize the conditions under which the new component/system will be used.

There is provided a system, method and computer readable medium that stores instructions that speeds up the testing of a features by allowing field-testing of a larger population and by spotting problems before they become failures. Also the system can accurately measure and characterize the conditions under which the new component/system will be used.

There is provided a system, method and computer readable medium that may assist OEMs in launching new systems and/or new features more quickly and with higher confidence that the new system will work as intended. This is done by using cost-effective and bandwidth efficient telemetry to monitor new systems and subsystems in large-scale field-trials.

The terms "system" and "feature" are used in an interchangeable manner. Although the following examples will refer to a new system (new truck system) they are applicable to a new feature (new vehicle feature).

Non-limiting examples of vehicle systems include engine, transmission, brakes/antilock brakes, electronic stability control, axle/driveline, suspension/ride height control, tires/tire inflation monitor/control, instrument panel/driver interface.

Non-limiting examples of features may include one or more components, sub-systems, and the like. For example—a new axel, a new controller, and the like. The feature may be a mechanical feature and/or an electronic feature.

The system may include vehicle monitors that may transmit over one or more networks information to a computer. The system may utilize Traffilog's "campaign" approach for collecting and processing field data, which is completely adaptable to different situations.

In this approach, trucks with the new systems (e.g. new engine, after treatment, brakes) are driven in large-scale (e.g. 100 to 1000 units) field trials with a vehicle monitors such as the Traffilog optimal observer campaign running on the telematics platform.

Figure 13:
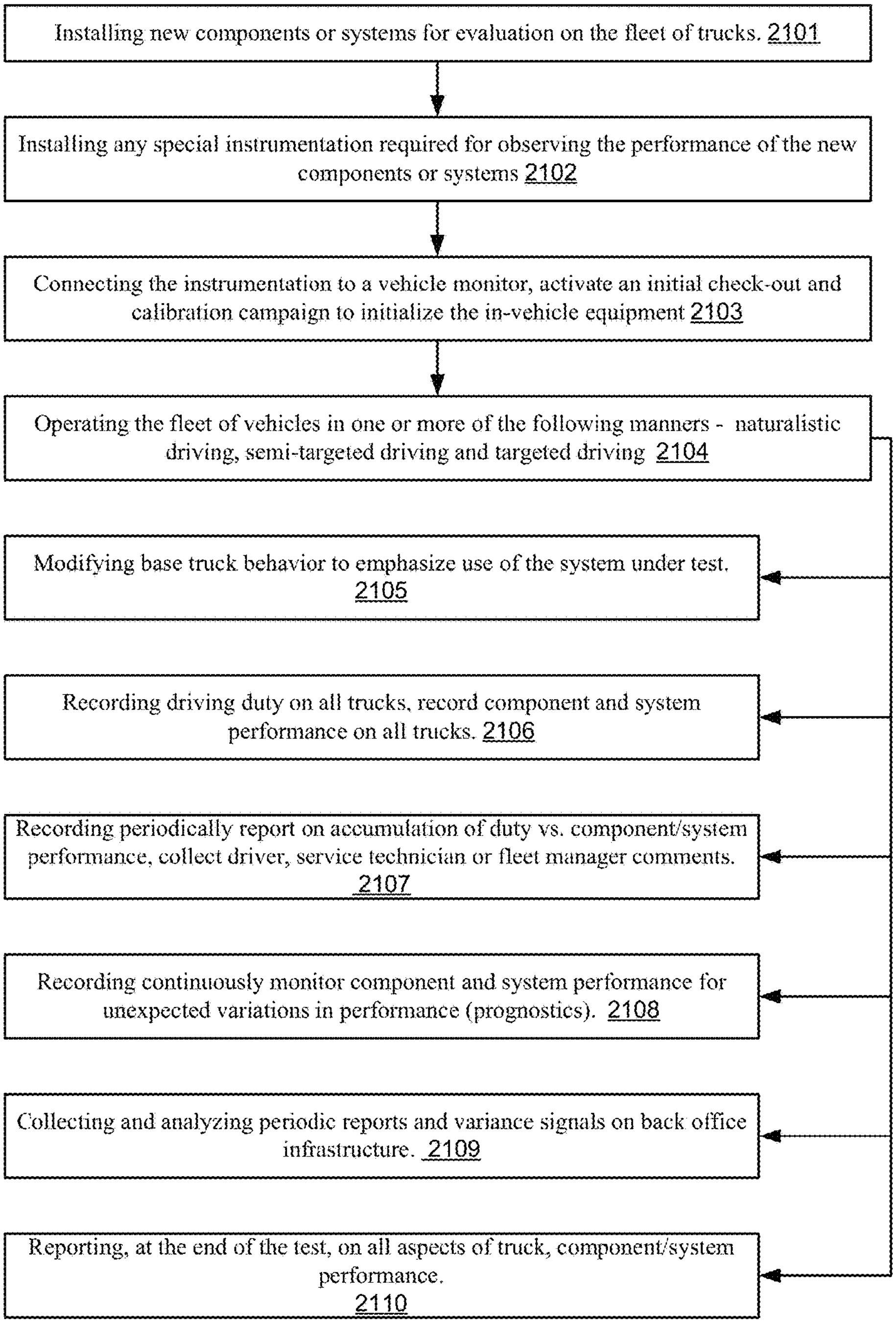
FIG. 13 illustrates a method according to an embodiment of the invention.

FIG. 13 illustrates method 2100 according to an embodiment of the invention.

Method 2100 include the following steps:

Step 2101 of installing new components or systems for evaluation on the fleet of trucks, Step 2102 of installing any special instrumentation required for observing the performance of the new components or systems. For example, on a truck fitted with a new drive axle, we may install an input shaft torque transducer to measure loading on gears and bearings related to driving torque. We may also install sensors to detect system failures (e.g. limit switches, software calculated limits on system performance).

Step 2103 of connecting the instrumentation to the Traffilog system, activate an initial check-out and calibration campaign to initialize the in-vehicle equipment.

Step 2103 may include:

a. Dynamically loaded campaign applet, b. Checks instrumentation connectivity and measurements during initial startup and calibration process, c. Cues technicians to perform actions to allow system check out (e.g. start engine, apply brakes, etc.), d. Delivers system status (go, no-go) and diagnostic information as needed, e. Signals to load main observer campaign on successful completion of initial check out.

Step 2104 of operating the fleet of vehicles in one or more of the following manners:

a. Naturalistic driving with no special feedback to the driver or fleet manager regarding the duty of the truck. In this case, the telematics system automatically collects the vehicle's operating condition and the performance of the component under test.

b. Semi-targeted driving with automatically generated special instructions to the driver when special driving conditions are required for testing (e.g. request the driver to alter normal driving patterns when environmental conditions allow testing additional conditions such as air temperature extremes or low traction roadway conditions). In this case, the system automatically records the vehicle's operating condition and compares this record to a list of required drive conditions. Based on this comparison the system may request the driver to operate the truck at a certain condition or perform a particular maneuver. For example, a test may require a certain amount of time with the engine operating at a given speed. Until the "drive at engine speed" target is met, the system maintains a prompt to remind the driver to hit the target speed, if possible.

c. Targeted driving with a closely controlled driving schedule to produce particular wear on components (e.g. fixed-route, fixed-load driving or test track driving). In this case, the system guides the driver through the required test schedule, by automatically keeping track of test schedule steps as they are accomplished.

For semi-targeted or targeted driving both the fleet manager and driver will have instructions from the system to assist in completing a test protocol. These instructions can be delivered by a number of mechanisms including web sites, smart phone apps or in-vehicle displays. The system may also direct drivers of field trials to use alternate routes or modify normal driving behavior (e.g. gear used on highway cruise) to accomplish complete test coverage. Drivers can be directed to accomplish a test protocol using a number of methods. For example, drivers can be given an online checklist of conditions to meet that is displayed on the vehicle's telematics system. The checklist indicates which conditions need to be met on a particular drive. As each condition is met it is checked off the list.

Regarding step 2104, little or no feedback is needed for driving in a completely naturalistic test case.

For semi-targeted or targeted driving both the fleet manager and driver will have instructions from the system to assist in completing a test protocol. These instructions can be delivered by a number of mechanisms including web sites, smart phone apps or in-vehicle displays. The system may also direct drivers of field trials to use alternate routes or modify normal driving behavior (e.g. gear used on highway cruise) to accomplish complete test coverage. Drivers can be directed to accomplish a test protocol using a number of methods. For example, drivers can be given an online checklist of conditions to meet that is displayed on the vehicle's telematics system. The checklist indicates which conditions need to be met on a particular drive. As each condition is met it is checked off the list.

To modify base vehicle behavior, the telematics system can intervene in normal operation or reprogram the required vehicle system to achieve the behavior change. This is done with either CAN bus messages or analog signals.

Step 2105 of modifying base truck behavior to emphasize use of the system under test (e.g. disable retarder to accumulate more use on the foundation brakes). To modify base vehicle behavior, the telematics system can intervene in normal operation or reprogram the required vehicle system to achieve the behavior change. This is done with either CAN bus messages or analog signals.

Regarding step 2105:

a. Data reductions techniques such as averaging or histogramming are used to reduce the amount of data sent over cellular data connections.

b. More sophisticated techniques such as optimal observers or model based observers can be used as part of the recording campaign.

c. Because the Traffilog system is dynamically reprogrammable while in operation, tests can be modified on-the-fly to account for variability of component/system performance or other factors.

d. Analyze the conditions under which the component/system is subjected to on the truck. Compare this with OEM engineering specifications for operating conditions. Report any variances.

Step 2106 of recording driving duty on all trucks, record component and system performance on all trucks.

Regarding step 2106:

a. Data from the truck can be sent out on a periodic basis, b. Data from the truck can be sent out on as-needed basis triggered by conditions on the truck, requests from a central server or other conditions, Step 2107 of recording periodically report on accumulation of duty vs. component/system performance, collect driver, service technician or fleet manager comments.

Regarding step 2107:

a. Use techniques similar to "Faster Product Improvement" to detect variances in component/system performance.

b. Signal the driver or fleet manager as appropriate if immediate action is needed.

Step 2108 of recording continuously monitor component and system performance for unexpected variations in performance (prognostics). When variations are detected, capture the circumstances of the variance, send a signal to indicate a variance is detected, schedule inspections or maintenance to learn the source of variance.

Step 2109 of collecting and analyzing periodic reports and variance signals on back office infrastructure.

Regarding steps 2108 and 2109:

a. Use cellular infrastructure and internet data transport to get data from the truck to the back-office infrastructure.

b. Normalize "as-driven" component/system performance back to "standard test" conditions using any of a number of techniques such as, collecting the number and severity of high-stress cycles and comparing to high-stress cycles on a standard test. The ability to use a large number of devices under test with accurately measured test conditions allows tests to be completed more quickly with better test coverage.

c. For cyclically stressed steel components, we can normalize measured duty in the truck by comparing actual stress cycles in the truck (number of cycles and stress levels) to known benchmark stress vs. cycle data. For other vehicle systems, such as brakes or clutches, a measure to total energy dissipated is a good measure for comparing actual truck data to benchmark data. For after treatment systems, accumulated time, mass flow, temperature, and chemical composition are good measures.

d. Test results and analysis tools can be available online with help desk type support, which allows a large number of users (product engineers) to quickly use the system with a minimum of training.

Step 2110 of reporting, at the end of the test, on all aspects of truck, component/system performance.

Method 2100 may include sending an alert when the monitoring system fails to start or run properly (self-test, watchdog functions).

The overall collection and analysis process may be useful in circumstances other than large-scale fleet tests.

For systems that require extreme test conditions that cannot be observed in normal field operation, tests can be accomplished in a laboratory capable of generating the extreme conditions, but with fixturing and instrumentation identical to that used in the fleet tests. This data is then easily combined with field test data to form a complete picture of the system's performance. When over-stress data from a laboratory test uses the same instrumentation as is used on field trials, that data can be treated as if it were generated on a truck in the field.

Field trial trucks may also carry multiple copies of a component or subsystem that are monitored during truck operation, but not being used online for truck operation. For example, a single field test truck may carry multiple ABS sensors mounted on an axle for vibration, shock and environmental testing although only one of the sensors is used in the online ABS system. If multiple active copies of the component under test are possible, compare results from components on the same truck to find variances. For example, temperature sensors should all read the same under cold soak conditions. Create events to capture and report mismatched readings.

Figure 14:
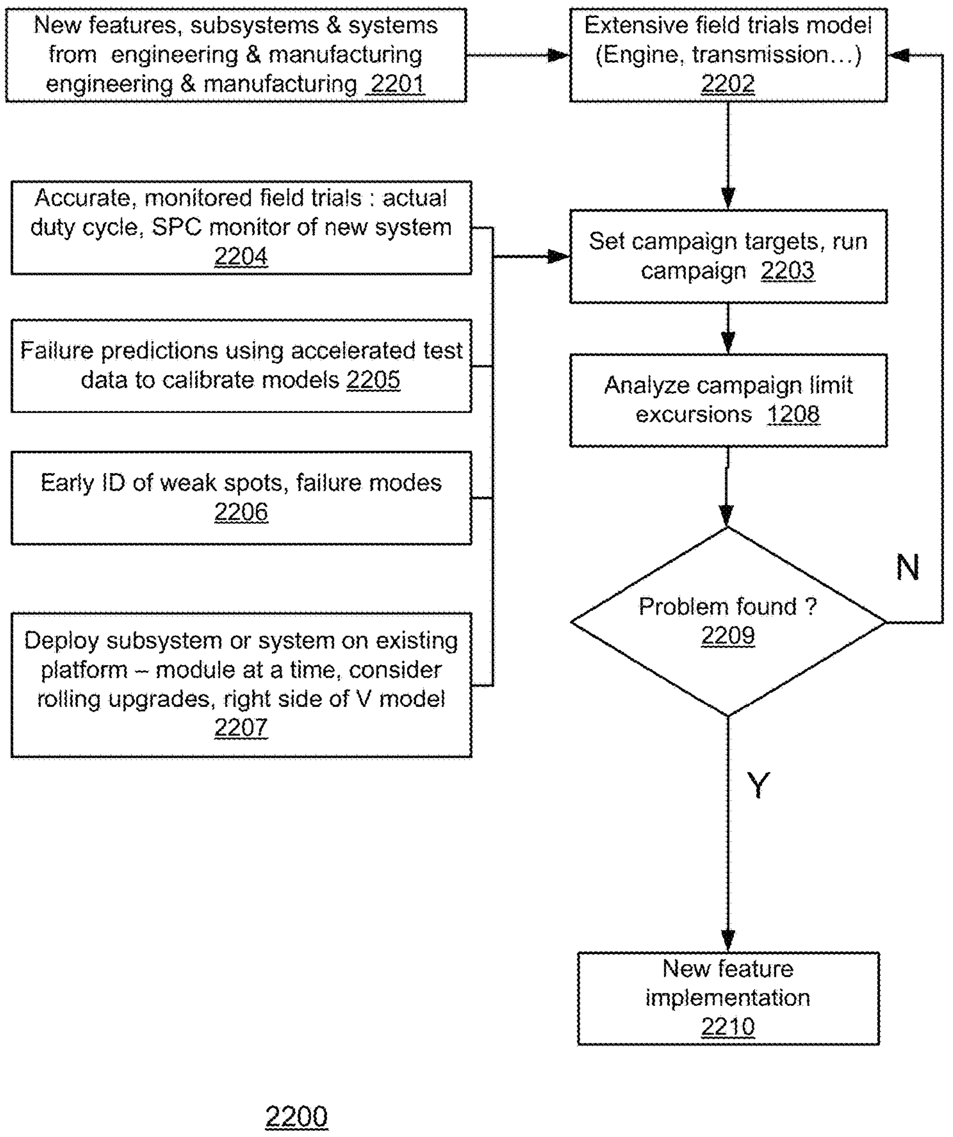
FIG. 14 illustrates a method according to an embodiment of the invention.

FIG. 14 illustrates method 2200 according to an embodiment of the invention.

Method 2200 includes steps 2201-2210.

Step 2201 includes fitting new features, subsystems and systems on the vehicle to be tested.

Step 2202 involves running the vehicle under test in a field trial possibly designed to stress the new feature, subsystem or system fitted in step 2201.

Step 2204 Sets expected values and tolerances of measured parameters related to the new feature, subsystem or system under test. These values determine if actions, alerts etc., are required during the field trial.

Step 2205 Sets expected failure levels of parameters related to the new feature, subsystem or system under test. When a component is exposed to operation at a failure level during a test an alert is generated even if the component's performance continues to be in range.

Step 2206 Sets tighter tolerances for in-range operation based on other test results indicating a possible weak spot. For example, if one truck in a test fleet a cooling system problem, in-range tolerances for coolant temperature may be changed for all trucks in the test fleet.

Step 2207 As a field trial progresses, and new or upgraded equipment is fitted to the vehicle, track these changes with corrected campaign targets. As a field trial progresses and the lower level of components and sub-systems have proven reliable move the testing and observation tasks to higher levels of the system. For example, once the engine turbocharging, fueling and cooling systems have been observed to meet targets move the testing emphasis to overall engine power and efficiency testing.

Step 2203 Based on campaign targets from multiple sources (steps 2202—2207) observe the vehicle's behavior and compare to targets.

Step 1208 Analyze observed limit excursions and determine if a problem is found. In most cases, a limit excursion indicates a problem, which is passed on to the next step. In some cases, we may apply additional logic to a limit excursion to reduce false problem indications. For instance many parameters may be out of range during test conditions not anticipated in the models and thresholds used in the campaign. For example, a vehicle start during and extreme cold-weather may trigger many out of range parameters, which can be ignored.

Step 2209 If a problem is found branch to step 2210. If no problem is found branch to step 2202.

Step 2210 Create new or modified features, subsystems and systems in response to problems found.

Figure 15:
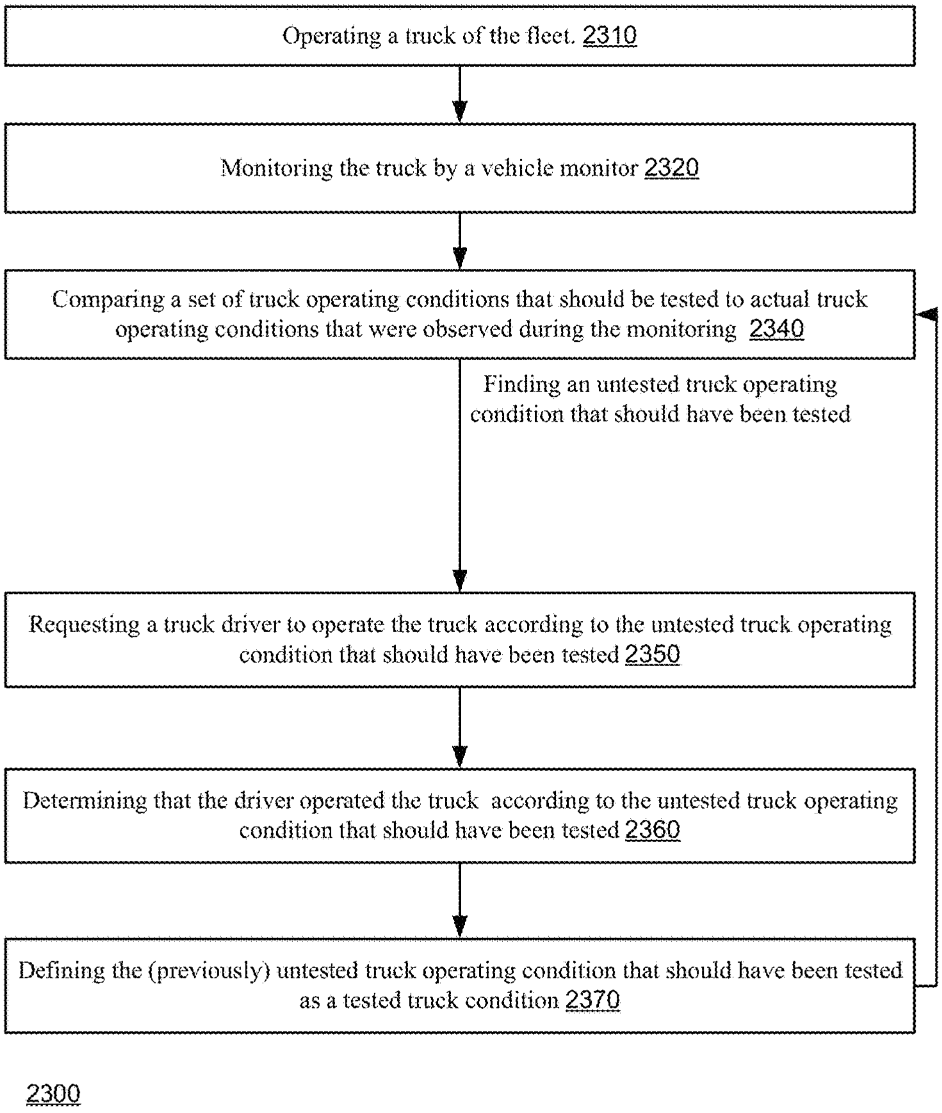
FIG. 15 illustrates a method according to an embodiment of the invention.

FIG. 15 illustrates method 2300 according to an embodiment of the invention.

Method 2300 guarantees that the truck will undergo a set of operating conditions that should be tested.

Method 2300 may include the steps of:

a. Step 2310 of operating a truck of a fleet of trucks.

b. Step 2320 of monitoring the truck by a vehicle monitor.

c. Step 2340 of comparing a set of truck operating conditions that should be tested to actual truck operation conditions that were observed during the monitoring. The comparison is aimed to determine whether there is an untested truck operating condition that should have been tested.

d. If finding an untested truck operating condition that should have been tested—then step 2340 is followed by step 2350 of requesting a truck driver to operate the truck according to the untested truck operating condition that should have been tested.

e. Step 2360 of determining that the driver operated the truck according to the untested truck operating condition that should have been tested. If the truck driver failed to operate the truck according to the untested truck operating condition that should have been tested—then the truck driver may receive notifications from the vehicle monitor and/or a control center or a third party may be notified about this problem. If the f. If the driver operated the truck according to the untested truck operating condition that should have been tested—then step 2360 is followed by step 2370 of defining the (previously) untested truck operating condition that should have been tested as a tested truck condition.

Step 2370 may be followed by step 2340.

Figure 16:
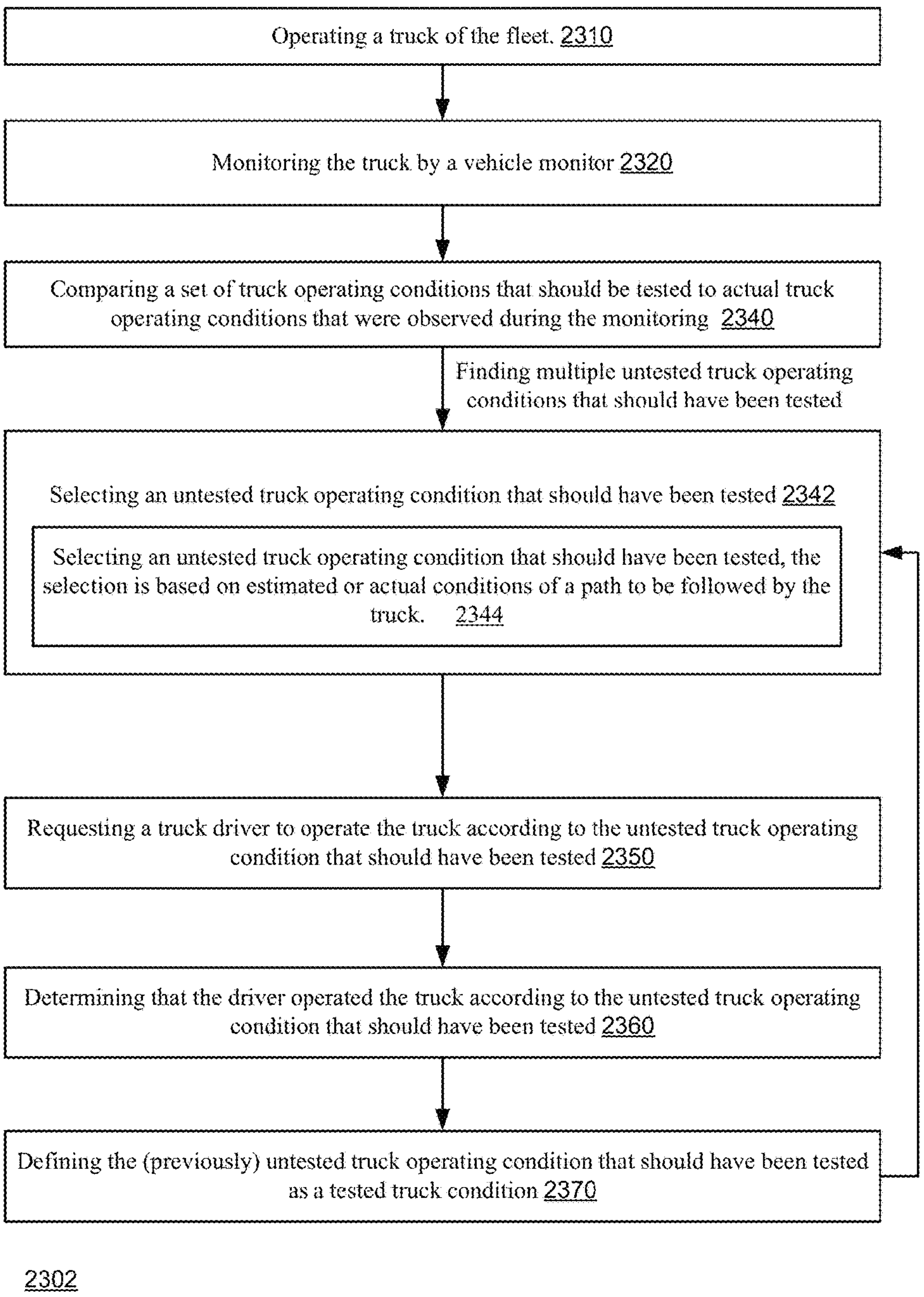
FIG. 16 illustrates a method according to an embodiment of the invention.

FIG. 16 illustrates method 2302 according to an embodiment of the invention.

Method 2302 guarantees that the truck will undergo a set of operating conditions that should be tested.

Method 2302 may include the steps of:

a. Step 2310 of operating a truck of a fleet of trucks.

b. Step 2320 of monitoring the truck by a vehicle monitor.

c. Step 2340 of comparing a set of truck operating conditions that should be tested to actual truck operation conditions that were observed during the monitoring. The comparison is aimed to determine whether there are multiple untested truck operating conditions that should have been tested.

d. If finding multiple untested truck operating conditions that should have been tested-then step 2340 is followed by step 2342 of selecting and untested truck operating condition out of the multiple untested truck operating conditions. The selecting can be performed according to any selection criterion, in a ransom manner, in a pseudo random manner, according to a predefined order of actual truck operation conditions, according to estimated and/or actual conditions of a path to be followed by the truck (step 2344). The estimated and/or actual conditions may be for example, positive slopes, negative slopes, horizontal path segments, curvature of a path segment, roughness of a path segment, and the like. The path that is followed by the truck can be known in advance (predefined path dictated to the driver of the truck), can be a path that is commonly used by one or more trucks of the fleet, and the like. The vehicle monitor can (based on characters of different paths segments of different paths) direct the truck driver to follow a certain path that includes path segments in which different truck operating conditions may be tested. The vehicle monitor may inform the driver before reaching a path segment which truck operating condition will be tested on that path segment. The vehicle monitor may be fed with path segments conditions and/or may store truck information from previous passes over the path segments and/or may receive information from other trucks of the fleet that passed over the paths segments. For example—a path segment that has a steep positive slope may be used to test low speed high moment propagation while a path segment that has a steep negative slope may be used to test the brakes of the vehicle and/or retarders.

e. Step 2342 is followed by 2350 of requesting a truck driver to operate the truck according to the untested truck operating condition that should have been tested.

f. Step 2360 of determining that the driver operated the truck according to the untested truck operating condition that should have been tested. If the truck driver failed to operate the truck according to the untested truck operating condition that should have been tested—then the truck driver may receive notifications from the vehicle monitor and/or a control center or a third party may be notified about this problem.

g. If the driver operated the truck according to the untested truck operating condition that should have been tested—then step 2360 is followed by step 2370 of defining the (previously) untested truck operating condition that should have been tested as a tested truck condition.

Step 2370 may be followed by step 2342.

Figure 17:
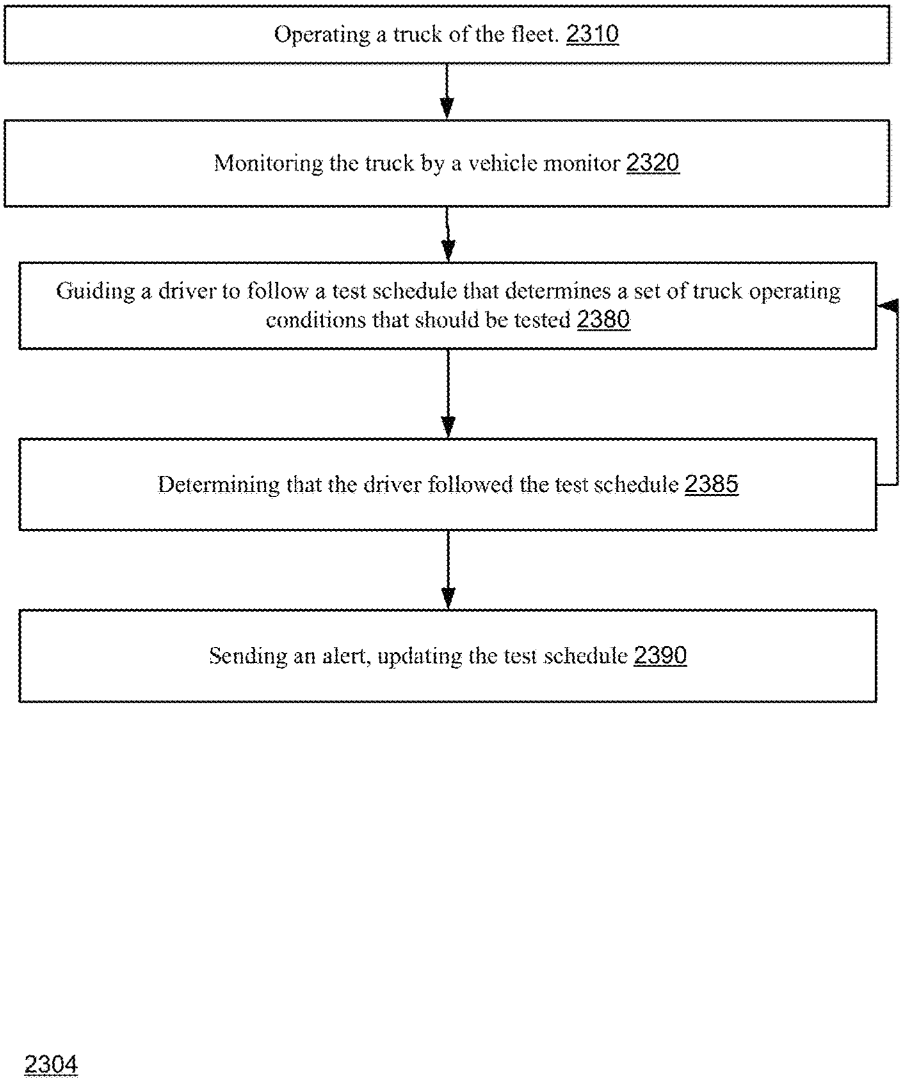
FIG. 17 illustrates a method according to an embodiment of the invention.

FIG. 17 illustrates method 2304 according to an embodiment of the invention.

Method 2304 guarantees that the truck will undergo a set of operating conditions that should be tested.

a. Step 2310 of operating a truck of a fleet of trucks.

b. Step 2320 of monitoring the truck by a vehicle monitor.

c. Step 2380 of guiding a driver to follow a test schedule that determines a set of truck operating conditions that should be tested. The guiding may include instructing the drive to operate the truck according to one truck operating conditions that should be tested at a time.

d. Step 2385 of determining that the driver followed the test schedule. If the truck driver failed to operate the truck according to the test schedule—then an alert may be generated (2390), the truck driver may receive notifications from the vehicle monitor and/or a control center or a third party may be notified about this problem.

Real Time Failure Analysis and Accurate Warranty Claim Assessment

On commercial vehicles, failed components and systems and subsequent warranty claims lead to customer dissatisfaction and costs for original equipment manufacturers (OEMs).

OEMs currently have little evidence other than a failed part and/or a DTC on which to judge the validity of a warranty claim. This lack of evidence leads to difficult relations between customers and OEMs.

The lack of evidence leads to difficult relations between customers and OEMs. Both parties are tempted to interpret the available evidence in the differently. The lack of evidence rarely leads to an optimal solution for both parties There is a growing need to provide a method and system that will enable to provide thorough understanding the cause of failures and subsequent warranty claims, OEMs can reduce unnecessary warranty claims and guide customers to products, usage processes and maintenance processes that will eliminate failures. Other interested parties include financing entities, suppliers, and fleets for a truck "health state" measure.

There is provided a system, method and computer readable medium that stores instructions that efficiently measures the duty cycle of the truck. In particular, the system measures load or force excursions that can cause disproportionately large damage to truck mechanical systems. With these measurements, both customers and OEMs can judge a particular truck's performance against warranted performance and durability.

Every system on a truck has a predicted life under "normal" operating conditions. When normal conditions are exceeded, OEMs typically try to deny warranty claims when failures occur. Getting to the root cause of a failure allows OEMs and customers to negotiate more accurately who pays and how to avoid failures in the future.

However, "normal" is difficult to define in detail without data. By having data showing actual use, both OEMs and customers can agree on "normal."

Figure 18:
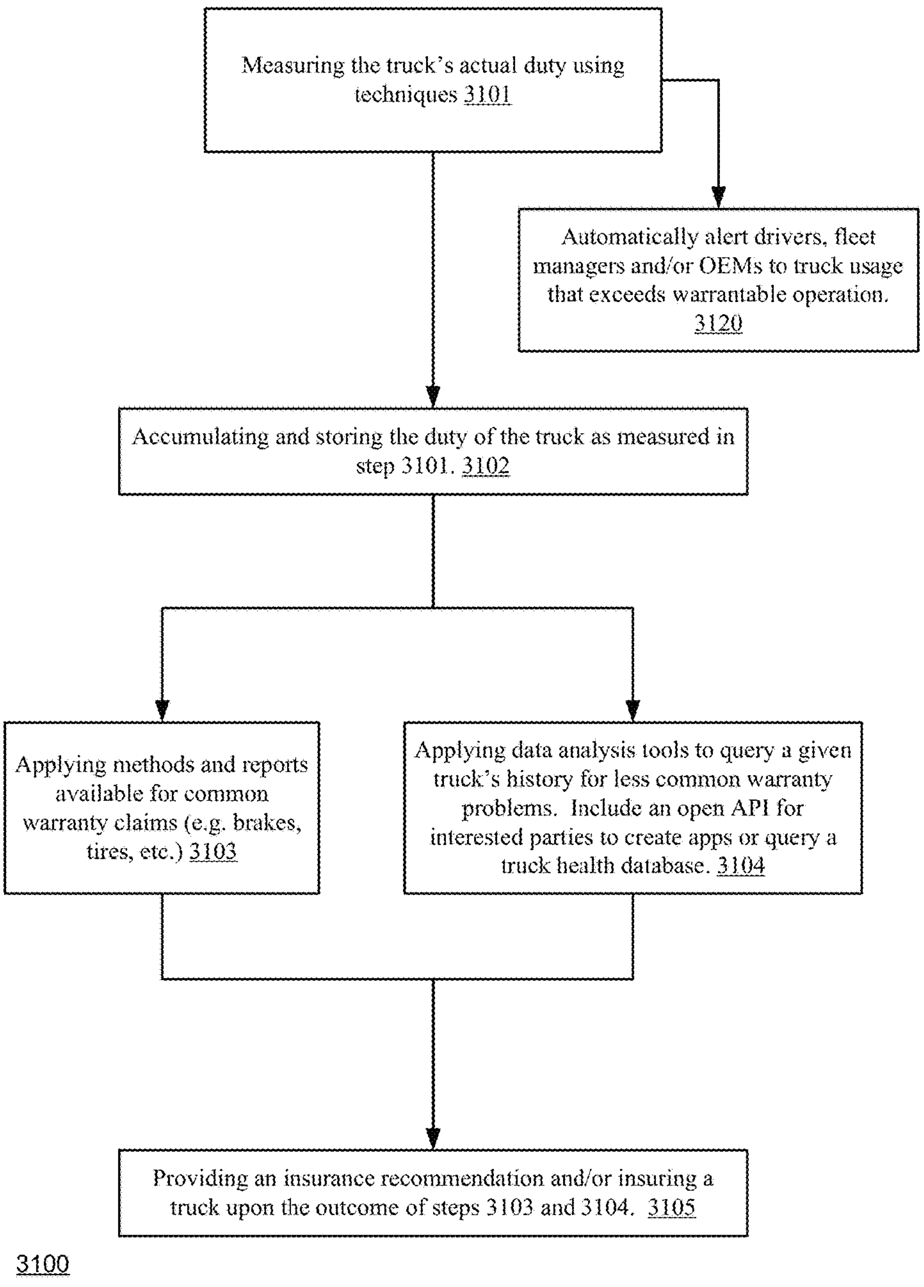
FIG. 18 illustrates a method according to an embodiment of the invention.

FIG. 18 illustrates method 3100 according to an embodiment of the invention.

Method 3100 include the following steps:

Step 3101 of measuring the truck's actual duty using techniques such as those described in the sections above titled "Faster Product Improvement," and/or "Faster New Feature Launch."

Step 3101 may be followed by step 3120 of automatically alert drivers, fleet managers and/or OEMs to truck usage that exceeds warrantable operation. For example, trucks operated in overloaded conditions are flagged immediately by the on-truck telematics unit. This unit calculates the vehicle mass from a number of quantities measured on the vehicle (e.g. ride height and air-suspension inflation pressure).

In another example, trucks that are specified for freeway usage with a maximum sustained grade of +/−3% are flagged as out of warranty coverage when operation in state highway conditions +/−6% are detected.

The determination of time on grade can be measured directly using a 3-axis accelerometer and a speedometer on the vehicle (when the road speed is not changing the average composite force vector from the accelerometer will have magnitude of 1G and indicate the grade that the truck is on, averaging removes the effect of bumps in the road). Time on grade can also be determined from GPS position and a lookup on a topographical map to determine roadway grade.

Step 3101 may be followed by step 3102 of accumulating and storing the duty of the truck as measured in step 3101.

Step 3102 may be followed by steps 3103 and 3104.

Step 3103 may include applying methods and reports available for common warranty claims (e.g. brakes, tires, etc.). Apply data from external warranty claim system to understand what are the top warranty items. Apply data from external warranty claim system to better understand the relationship between truck diagnosis and warranty claims.

Step 3103 may include having predefined (even standard) analysis methods and reports available for common warranty claims (e.g. brakes, tires, etc.) that are automatically populated by measured data from the truck in question. For example, in understanding tire failures, TMC RP-216B describes the industry standard classifications for tire failures, which can be the basis for classifying failures. The classified failures in conjunction with a detailed understanding of the truck's actual duty (step 2, above) can lead to understanding the correlation between a particular pattern of truck duty and tire failures. This is done by looking for a statistical correlation between measured parameters describing the truck and/or the truck's duty and a particular type of failure.

Step 3104 may include applying data analysis tools to query a given truck's history for less common warranty problems. Include an open API for interested parties to create apps or query a truck health database. Apply data from external warranty claim system to understand what are the top warranty items. Apply data from external warranty claim system to better understand the relationship between truck diagnosis and warranty claims.

Steps 3103 and 3104 may be followed by step 3105 of providing a warranty recommendation and/or insuring a truck upon the outcome of steps 3103 and 3104.

Many warranty claims arise from abuse of the truck due to overloading or operation not included in the truck's application approval (e.g. excessive grade, unpaved roads).

Referring to step 3103—the information may be provided in one of the following formats:

A standard report related to overloading might include: Average laden GCW, Maximum operating GCW observed, Hours of operation over rated GCW A standard report related to operation outside of application approved limits might include: Ton-miles of operation in non-approved conditions, Mileage of operation on rough roads and Mileage of operation on excessive grades.

Other abuse conditions may include over speeding of engine, driveline or both, over heating due to overload, over pressure of oil on cold start, lack of maintenance, overload of compressor due to extra trailers or leaks, under inflation of tires, clutch abuse, gearbox forced shifts, missed or inappropriate DPF regeneration.

Truck "wear state" or "health state" estimation can be used for a. Finance/Portfolio value measures, b. Value measure of assets under finance, c. Actual value of capital assets (not estimated or modeled, e.g. residual values)

d. Regulators/Safety Inspectors—interest in emissions compliance or safety, e. Industry consortium—understand truck performance, f. Aftermarket and parts suppliers—interest in component performance, g. Government—Tax and toll collection purposes.

This insurance system is robust against outages that may compromise the integrity or coverage of data from a given truck.

Ultimately, the execution of method 3100 may lead to new business models where customers pay for the use of a truck based on the duty cycle of the mission where OEMs can influence the choice of truck for the mission (power by the hour). Other new business models include: insurance-like model, variable/extended warranty offering, warranty deletion option, financing options based on usage, and a discount for using the online system.

Having evidence of a truck's actual usage to determine the root cause of a failure (e.g. OEM related flaw or customer abuse of truck).

By having good root cause determination of failures, customers and OEMs can work to optimize truck cost and performance, which saves money for both parties.

Figure 19:
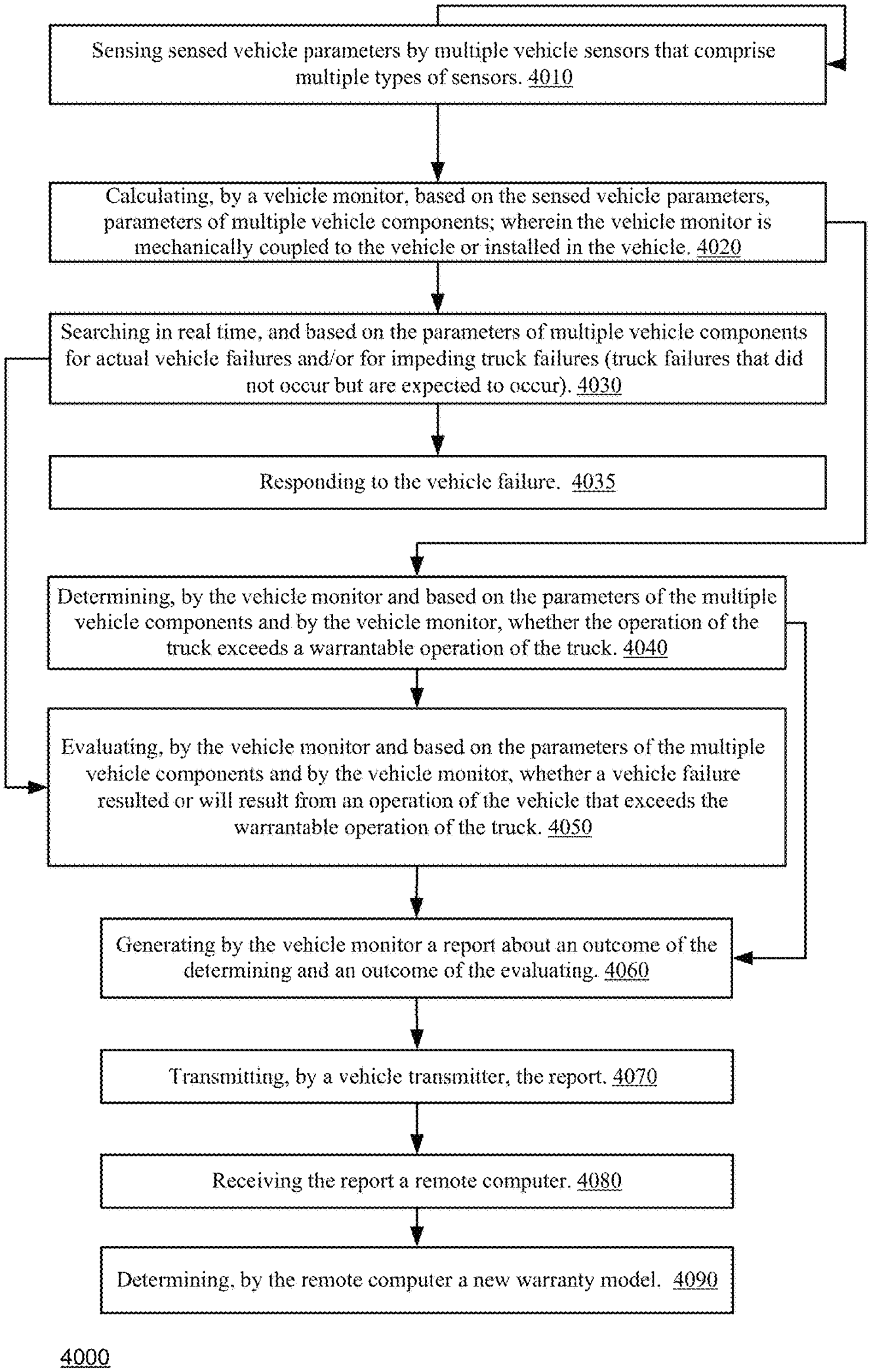
FIG. 19 illustrates a method according to an embodiment of the invention.

FIG. 19 illustrates method 4000 according to an embodiment of the invention.

Method 4000 may be used for failure analysis and warranty claim assessment.

Method 4000 may include:

Step 4010 of sensing sensed vehicle parameters by multiple vehicle sensors that comprise multiple types of sensors.

Step 4020 of calculating, by a vehicle monitor, based on the sensed vehicle parameters, parameters of multiple vehicle components; wherein the vehicle monitor is mechanically coupled to the vehicle or installed in the vehicle. The sensed vehicle parameters may be duty related parameters and method 400 may include determining by the vehicle monitor, based on the parameters of multiple vehicle components, an actual wear of the vehicle.

Step 4030 of searching in real time, and based on the parameters of multiple vehicle components for actual vehicle failures and/or for impeding truck failures (truck failures that did not occur but are expected to occur).

If an actual vehicle failure and/or for impeding truck failure is detected then step 4030 may be followed by step 4035 of responding to the vehicle failure. Step 4035 may include at least one of the following:

a. Generating, by the vehicle monitor and in real time, an alert about the vehicle failure.

b. Generating by the vehicle monitor and in real time an alert about an expected vehicle failure before the vehicle failure occurs.

c. Instructing the vehicle, by the vehicle monitor, to change a vehicle parameter if the vehicle monitor determines that a vehicle failure occurs or if a vehicle failure is impeding.

d. Informing, when the truck failure is a truck system failure and by the vehicle monitor, a vehicle controller that is responsible to the vehicle system about the vehicle system failure.

Step 4040 of determining, by the vehicle monitor and based on the parameters of the multiple vehicle components and by the vehicle monitor, whether the operation of the truck exceeds a warrantable operation of the truck.

Step 4050 of evaluating, by the vehicle monitor and based on the parameters of the multiple vehicle components and by the vehicle monitor, whether a vehicle failure resulted or will result from an operation of the vehicle that exceeds the warrantable operation of the truck.

Step 4050 may include searching for a correlation between the vehicle failure and a pattern of a usage of the vehicle.

Step 4060 of generating by the vehicle monitor a report about an outcome of the determining and an outcome of the evaluating.

Step 4070 of transmitting, by a vehicle transmitter, the report. The size of the report is a fraction (for example less than 1/100 or 1/1000 or 1/10000 of 1/1,000,000) of the aggregate size of the sensed vehicle parameters.

Step 4080 of receiving the report a remote computer.

Step 4090 of determining, by the remote computer a new warranty model. Step 4090 may be executed by the vehicle monitor.

Service Improvement by Better Incoming Diagnosis Data, Problem Specific Training and Technician Feedback The trucking industry in the Americas is suffering an acute shortage of qualified service technicians.

Most repair shops rely on training and certification of technicians to improve performance.

Training and certification are a good starting point, but don't measure how a technician actually uses the knowledge gained in training.

It has been found that by tracking and accurately rating each technician's performance, the industry can help technicians do a better job and create a professional standing for technicians that in-turn will help recruit new technicians.

By improving the tools that technicians have to diagnose and repair a truck, technician effectiveness improves.

Original equipment manufacturers (OEMs) that use these improvements will increase repair shop market-share and improve overall truck brand market value.

There are provided systems, methods and computer readable medium that stores instructions for accurately rating a technician's performance on each job and providing accurate training advice. This is done by measuring the technician's use of resources on a job, normalized by the difficulty of the job. This normalized measure helps illustrate the technician's performance correctly regardless of the difficulty of the job. These normalized measures also, allow a technician to compare their performance to others doing similar work.

Figure 20:
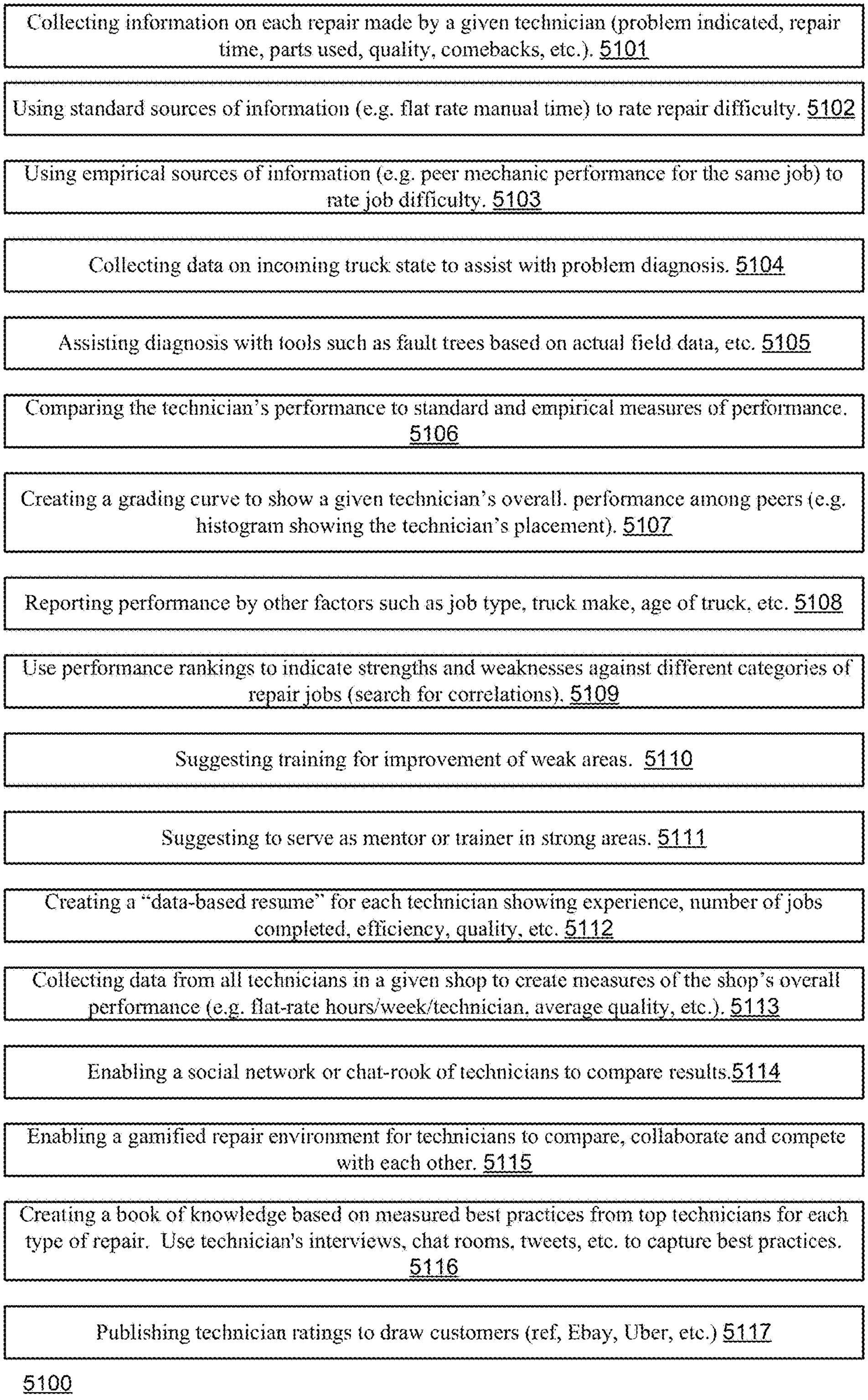
FIG. 20 illustrates a method according to an embodiment of the invention.

FIG. 20 illustrates method 5100 according to an embodiment of the invention.

Step 5101 provides information used for both ranking the difficulty of the repair job and ranking the technician's performance.

Information on the incoming truck's state (problem indicated, etc.) from steps 5101 and 5104 is used with information from steps 5102 and 5103 to rank the difficulty of the job (perhaps this should be shown as a step of its own).

Step 5106 compares information from step 5101 related to the mechanic's performance (repair time, parts used, quality, comebacks, etc.) to information from the ranking of difficulty to rank the technician's performance.

Method 5100 may include the following steps:

Step 5101 of collecting information on each repair made by a given technician (problem indicated, repair time, parts used, quality, comebacks, etc.).

Step 5102 of using standard sources of information (e.g. flat rate manual time) to rate repair difficulty.

Step 5103 of using empirical sources of information (e.g. peer mechanic performance for the same job) to rate job difficulty.

Step 5104 of collecting data on incoming truck state to assist with problem diagnosis.

Step 5105 of assisting diagnosis with tools such as fault trees based on actual field data, etc.

Step 5106 of comparing the technician's performance to standard and empirical measures of performance.

Step 5107 of creating a grading curve to show a given technician's overall. performance among peers (e.g. histogram showing the technician's placement).

Step 5108 of reporting performance by other factors such as job type, truck make, age of truck, etc.

Step 5109 of use performance rankings to indicate strengths and weaknesses against different categories of repair jobs (search for correlations).

Step 5110 of suggesting training for improvement of weak areas identified in step 5109.

Step 5111 of suggesting to serve as mentor or trainer in strong areas as identified in step 5109.

Step 5112 of creating a "data-based resume" for each technician showing experience, number of jobs completed, efficiency, quality, etc.

Step 5113 of collecting data from all technicians in a given shop to create measures of the shop's overall performance (e.g. flat-rate hours/week/technician, average quality, etc.).

Step 5114 of enabling a social network or chat-rook of technicians to compare results.

Step 5115 of enabling a gamified repair environment for technicians to compare, collaborate and compete with each other.

Step 5116 of creating a book of knowledge based on measured best practices from top technicians for each type of repair. Use technician's interviews, chat rooms, tweets, etc. to capture best practices.

Step 5117 of publishing technician ratings to draw customers (ref, Ebay, Uber, etc.).

Step 5101 may include collecting information from available sources to characterize the technician's performance on each repair. This includes information from a variety of sources such as, vehicle diagnostic codes, driver comments, repair orders, time and material usage trackers, OEM service manuals, etc.

This step may include showing flow of data from driver point of view, truck point of view, technician point of view, show how flows intersect during a repair event.]

Steps 5102 and 5103 (Use standard and empirical sources of information to rate the job difficulty) may include estimating job difficulty by combining one or more of the following parameters:

a. Flat-rate manual time (higher is generally more difficult)

b. Difference between flat-rate time and repair time for the technician in question and for the average of population of technicians (bigger differences are generally more difficult), c. Technician, service writer, shop manager opinions from surveys or social media, d. Variability of repair time for the technician in question and for the population of technicians (higher variability is more difficult), e. Number of parts required (more parts means higher difficulty), f. Number system/sub-systems affected (more means higher difficulty)

The information mentioned above ((a)-(f)) may be combined in a number of ways:

a. Sum or weighted sum of the parameters, b. Dimensionless or dimensioned ratios of the parameters, c. Best fit using multiple regression of sub-tasks in each repair job against overall difficulty or vice versa.

Step 5104 of collecting Data on incoming truck state may include:

1. Collect driver's comments,
2. Collect truck base information (VIN, model year, model, driveline, other options, etc.)
3. Collect OBD DTCs,
4. Collect recent usage history (loads, routes, driver history of truck abuse, driver history of repairs needed on their truck, etc.), include data from onboard telematics systems, Collect repair history of truck and maintenance schedule.

Step 5105 of assist diagnostics may include:

1. Create a fault tree based on data in step 5104 and technician input,
2. The fault tree can be guided by truck OEM diagnosis charts,
3. The fault tree can be modified by actual repair histories (add or trim branches as guided by field experience).
4. The fault tree can show probabilities associated with each branch.

Step 5106 of Compare technician's performance to standard and empirical measures of performance may include:

1. Compare technician's resource usage (time, parts, consumables) to flat rate manual, estimator's manual (less usage is better),
2. Compare as in 1 with flat rate adjusted by field empirical field data, Compare technician's performance on this job to similar jobs they have done in the past.

Step 5107 of creating a grading curve to show a technician's performance vs peers may include:

1. Compare technicians individual repair or average repair performance to peers using performance-to-grade function that yields high, mid, and low grades in the desired proportions,
2. Use a histogram (grade vs. number of samples) to show a technician's performance:

a. vs. individual performances or average performances of peers b. vs. individual performances of themselves.

Step 5108 of Report technician performance against other factors may include:

a. report the technician's performance against other factors such as truck model, driveline configuration, truck age, truck mileage, etc., b. Search the space of other factors for correlations with performance.

Figure 21:
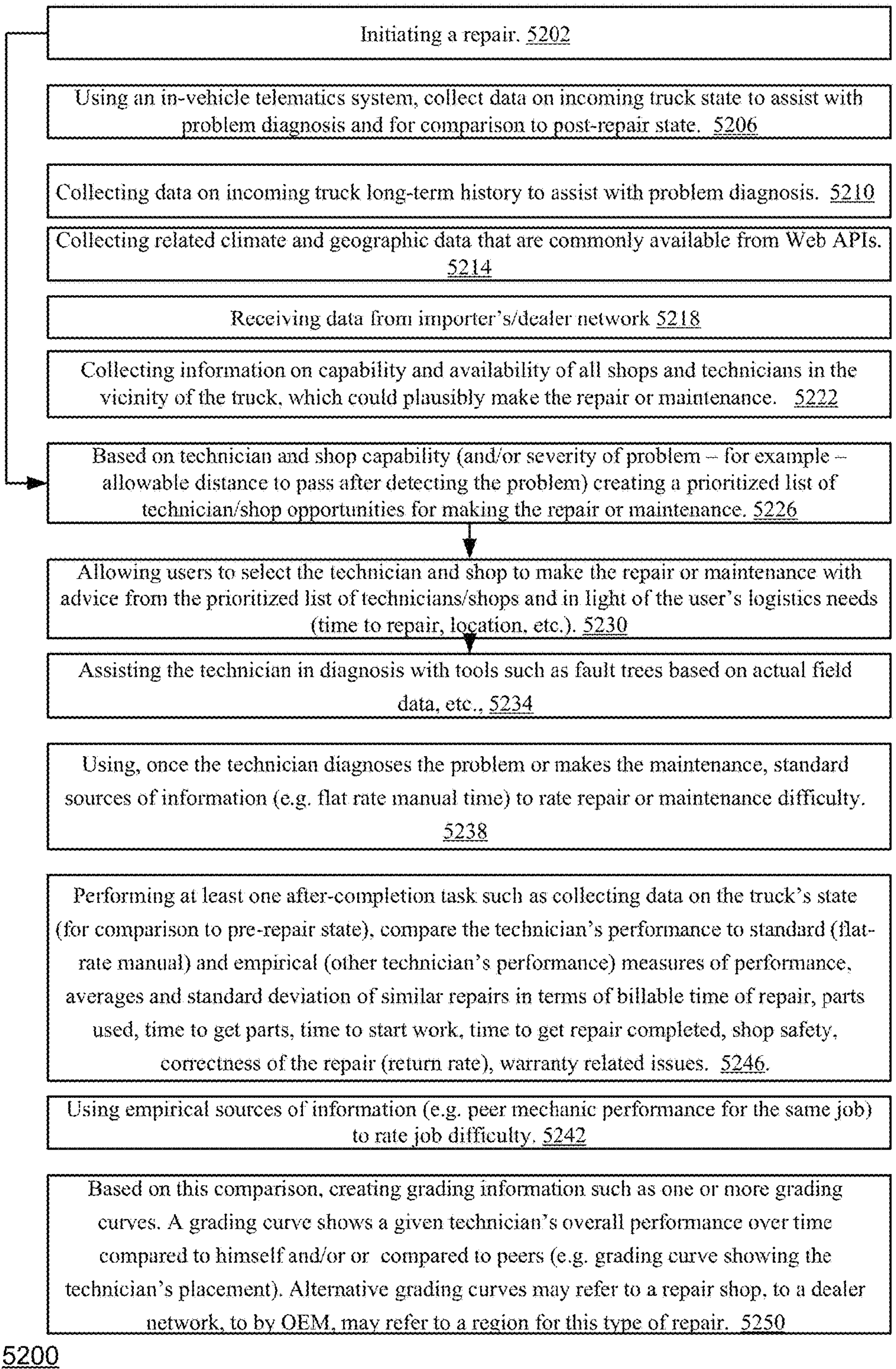
FIG. 21 illustrates a method according to an embodiment of the invention.

FIGS. 21-22 illustrate method 5200 according to an embodiment of the invention. Method 5200 includes steps 5202, 5206, 5210, 5214, 5218, 5222, 5226, 5230, 5234, 5238, 5242, 5246, 5250, 5254, 5258, 5262, 5266, 5270, 5274, 5278, 5280, 5281, 5282, 8283 and 5284:

Initiating a repair, when a truck is in need of repair or maintenance, we can initiate a repair or maintenance event from any of a number of different sources: high priority event detected by the Traffilog telematics system (e.g. DTC), driver complaint, maintenance flag, inspection failure, etc. When a repair or maintenance event is initiated proceed with the following steps. Each truck repair event is tracked as a transaction and all associated data described below is maintained as part of the transaction record.

Using an in-vehicle telematics system, collect data on incoming truck state to assist with problem diagnosis and for comparison to post-repair state. Incoming data includes: recent truck background data (uptime, core truck efficiency, duty cycle/mission, etc.), DTCs, and driver abuse (the story that the driver never tells . . . ).

Collecting data on incoming truck long-term history (time in service, history of duty cycle/mission, repair history, environment/climate, etc.) to assist with problem diagnosis. From SAP, TMV, or similar, access data using commonly available web APIs. Collect related climate and geographic data that are commonly available from Web APIs. Receive data from importer's/dealer network database, such as the Iveco database in Europe.

Collecting information on capability and availability of all shops and technicians in the vicinity of the truck, which could plausibly make the repair or maintenance. Information on technician capability includes: each repair made by a given technician (problem indicated, repair time, parts used, quality, comebacks, etc.), overall technician ranking and technician ranking related to the current repair job. Information on shop capability includes history of dealing with similar repair or maintenance events, availability of technician time and shop resources to make the repair or maintenance. Based on technician and shop capability create a prioritized list of technician/shop opportunities for making the repair or maintenance.

Allowing users to select the technician and shop to make the repair or maintenance with advice from the prioritized list of technicians/shops and in light of the user's logistics needs (time to repair, location, etc.).

Assisting the technician in diagnosis with tools such as fault trees based on actual field data, etc., (e.g. CNH Assist, share fault tree from current repair, each repair builds on previous fault tree) <Automatic improvement of fault tree based on transaction data and machine learning techniques.>

Using, once the technician diagnoses the problem or makes the maintenance, standard sources of information (e.g. flat rate manual time) to rate repair or maintenance difficulty.

Using empirical sources of information (e.g. peer mechanic performance for the same job) to rate job difficulty.

Performing at least one after-completion tasks (After completion of the job): collecting data on the truck's state (for comparison to pre-repair state), compare the technician's performance to standard (flat-rate manual) and empirical (other technician's performance) measures of performance, averages and standard deviation of similar repairs in terms of billable time of repair, parts used, time to get parts, time to start work, time to get repair completed, shop safety, correctness of the repair (return rate), warranty related issues (time limit, OEM parts, etc.).

Based on this comparison, creating a grading curve to show a given technician's overall performance over time compared to himself and compared to peers (e.g. grading curve showing the technician's placement), by repair shop, by dealer network, by OEM, by region for this type of repair. Share this comparison with the technician and other authorized, interested parties. For example, a particular technician may be ranked at the top of all technicians with respect to brake repairs, but due to his lack of experience in engine repairs his overall rating may be very low. So it is important to show an overall rating that covers repairs made to any system on the truck in the correct context for technicians that only work on certain truck systems. It is also important to show each technician's performance over time to illustrate how the technician's work improves with experience.

Also, if sufficient data is available, reporting technician performance by other factors such as job type, truck make, age of truck, etc., Using performance rankings to indicate strengths and weaknesses of each technician against different categories of repair jobs (search for correlations). Categories of repair jobs include: inspections, brakes, tires, electrical lighting, electrical accessories, transmission, engine, chassis, trailer, suspension, axle, driveline, interior/seating, etc. Report strengths and weaknesses to the technician on a periodic basis.

Given the truck's incoming state and history described above, suggesting ways to understand root cause of the need for repair, this may involve feedback to the driver, fleet manager, or OEM.

Suggesting training for technician improvement of weak areas identified in step 12, "top three" report card, and similar Traffilog report to drivers, based on performance. Handle this as private information for authorized use only. The report would typically show improvements over time, show problem areas and show ranking among other technicians.

Suggesting that a particular technician could serve as mentor or trainer to less-capable technicians, in strong areas Creating a "data-based resume" for each technician showing experience, number of jobs completed, efficiency, quality, etc. for the technician to use as a basis of job certifications or other purposes.

Collecting data from all technicians in a given shop to create measures of the shop's overall performance (e.g. flat-rate hours/week/technician, average quality, etc.) workshop tools availability, efficiency getting parts, parts availability, and safety.

Enabling a social network or chat-room of technicians to compare results. Of particular interest in the social network, flag unusual faults/repairs, flag errors in training, flag errors in fault-trees, etc. Enable technicians to compare performance results. Enable a technician ranking system based on experience, quality, efficiency, etc. (rookie, some experience (newbie), much experience (qualified technician), top experience (master), most experience (trainer, foreman)).

Enabling a gamified repair environment for technicians to compare, collaborate and compete with each other. This could be enabled with a real-time status ("battlefield") display of an entire shop indicating location of each job, assigned technician, job difficulty, time used, parts used, technician comments.

Creating a book of knowledge (Wiki structure?) based on measured best practices from top technicians for each type of repair. Use technician's interviews, chat rooms, tweets, etc. to capture best practices. This is the basis of a continuous the improvement process.

Publishing technician and shop ratings to draw customers (ref, Ebay, Uber, etc.)

Figure 23:
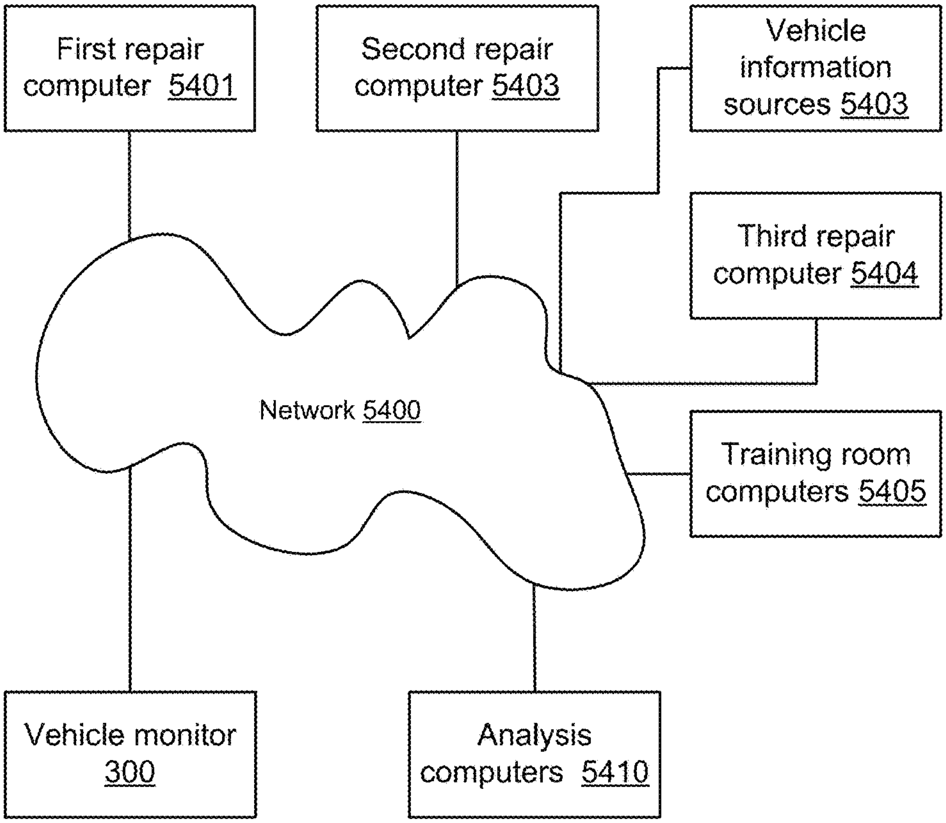
FIG. 23 illustrates a system according to an embodiment of the invention.

FIG. 23 illustrates a system that may include a vehicle monitor 300, analysis computer 5410, first repair computer 5401, second repair computer 5403, vehicle information sources 5403, third repair computer 5404 and training room computers 5405, that are coupled via network 5400.

The number of computers, their types and/or their connectivity may vary from those illustrated in FIG. 23. The computers may be servers, desktop computers, laptop computers, dedicated computers, and the like.

Any of the repair computers are computers that are used during the repair of a vehicle failure. They may be computerized vehicle diagnostic systems that are tailored to a specific brand or manufacturer of vehicles, can be a multipurpose diagnostic tool, can be a computer that is used to report repairs and/or monitor the repair—such as monitoring time of repair, parts that are used to repair the vehicle failure, and the like.

The vehicle monitor may provide information about the truck failure, about the status of the truck before and/or after the truck failure, prove inputs about the impact of the repair—whether the repair succeeded or failed, whether the repair partially succeeded, the amount of improvement in the vehicle status due to the repair, and the like.

The analysis computer 5410 may analyze information from the first till third repair computers, from the vehicle monitor 300, from the vehicle information sources 5403 and generate the technician grade or any other grading or comparison information related to the repair, technician, shop, and the like.

The system of FIG. 23 is an example of a system that includes one or more computers such as servers, laptops, desktop computers, and the like that distributed cog information from available sources to characterize the technician's performance on each repair.

This includes information from a variety of sources such as, vehicle diagnostic codes, driver comments, repair orders, time and material usage trackers, OEM service manuals, etc.

The information sources may be, for example, sources related to the truck diagnosis and repair, technician history database, analysis algorithms, shop management database, repair order time, parts, supplies database and the like.

The one or more computer may host various types of software such as report generating software, display software, apps on mobile platforms, etc.

The system may execute instructions linking data from a number of sources related to the truck diagnosis and repair, technician history database, analysis algorithms, report generating software, display software, apps on mobile platforms, etc.

The system may provide improved incoming diagnosis data and truck history. This helps technicians more quickly diagnose problems (from shop management database, repair order time, parts, supplies) (normalizing factors include: flat rate manual time, historical performance by other technicians, service manager input, etc.)

The system may provide specialized training, using conventional training materials such as shop manuals, computer-based instruction, video clips, etc. (how) when a technician is faced with a repair they have never made before.

The system may provide an ECU dump analyzer responsive to short-term trends, long-term trends, statistics, etc. (read ECU state, event history and interpret what happened before and during failure).

The system includes an over the air diagnosis capability (please elaborate) that allows a technician to observe truck operation remotely over a wireless link. Allow the technician to observe in near-real time what the truck is doing while on the road. Allow a conversation between the truck driver and the technician. Such a system may include a CAN bus gateway that conducts CAN bus messages local to the truck across the wireless internet to a CAN bus analyzer or diagnostic tool, or to a server-based CAN bus analyzer. The system may include an over-the-air patch capability that allows a technician to push a diagnostic or limp-home code to electronic controllers on the truck. For example, when a problem is detected in the urea doser in a selective catalytic reduction exhaust after treatment system, the system may automatically push limp-home software to the truck. In this case the doser is operated to slightly over-dose the SCR catalyst with urea, which allows the truck to remain in compliance with emissions regulations at the cost higher urea fluid consumption. Once the problem with the doser is repaired, normal operating code is restored. In another example, the technician may need to collect more detailed information on the truck's operation to make a correct diagnosis. In this case, the system may automatically push diagnostic software to the truck, which transmits the needed information.

The system provides a measure of overall shop performance (described above) (please elaborate) by observing the performance of all the technicians in the shop. Similar to mechanic performance, measure key performance indicators of the overall shop (e.g. billable hours, flat rate time vs real time, overhead costs, etc.)

The system can provide measures of shop support activities such as parts procurement, warranty claim clearance rates, etc.

The proposed system measures a technician's performance on each job, suggests training for improvement and allows a technician to compare their performance to others doing similar work.

The system also includes a number of tools to speed up problem diagnosis, and reduce repair time. These include: incoming diagnostics from truck to be repaired, ECU dump analyzer, and as needed training, delivered on the job.

The system improves the technician's capability and therefore their professional standing. This also improves results for repair customers and shop owners.

The proposed system measures a technician's performance on each job, suggests training for improvement and allows a technician to compare their performance to others doing similar work.

The system also includes a number of tools to speed up problem diagnosis, and reduce repair time. These include: incoming diagnostics from truck to be repaired, ECU dump analyzer, and as needed training, delivered on the job.

Figure 24:
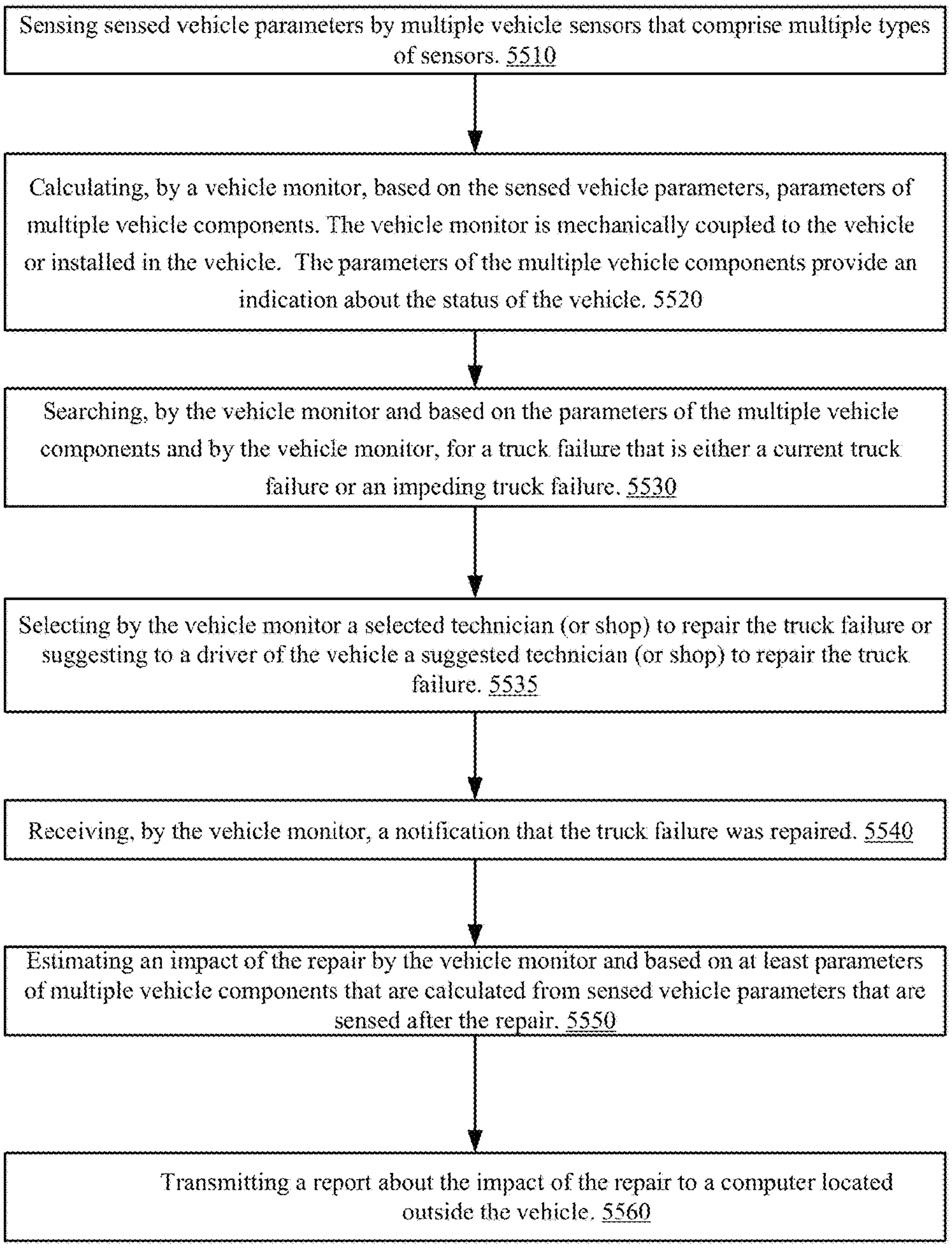
FIG. 24 illustrates a method according to an embodiment of the invention.

FIG. 24 illustrates method 5500 according to an embodiment of the invention.

Method 5500 may be used for failure analysis and technician assessment.

Method 5500 may include the steps of:

Step 5510 of sensing sensed vehicle parameters by multiple vehicle sensors that comprise multiple types of sensors.

Step 5520 of calculating, by a vehicle monitor, based on the sensed vehicle parameters, parameters of multiple vehicle components. The vehicle monitor is mechanically coupled to the vehicle or installed in the vehicle. The parameters of the multiple vehicle components provide an indication about the status of the vehicle.

Step 5530 of searching, by the vehicle monitor and based on the parameters of the multiple vehicle components and by the vehicle monitor, for a truck failure that is either a current truck failure or an impeding truck failure.

Step 5535 of selecting by the vehicle monitor a selected technician (or shop) to repair the truck failure or suggesting to a driver of the vehicle a suggested technician (or shop) to repair the truck failure.

Step 5540 of receiving, by the vehicle monitor, a notification that the truck failure was repaired.

Step 5550 of estimating an impact of the repair by the vehicle monitor and based on at least parameters of multiple vehicle components that are calculated from sensed vehicle parameters that are sensed after the repair.

Step 5560 of transmitting a report about the impact of the repair to a computer located outside the vehicle.

Step 5550 may include comparing between a status of the vehicle before the repair and a status of the vehicle after the repair.

Step 5535 may include at least one of the following:

a. Receiving or generating, by the vehicle monitor, repair information about locations and technical skills of multiple technicians; and selecting by the vehicle monitor a selected technician based on the technician information and a location of the vehicle. The technical skills of the multiple technicians may be related to a repair of the truck failure.

b. Receiving or generating, by the vehicle monitor, repair information about locations and technical skills of multiple technicians; and selecting by the vehicle monitor a selected technician based on at least one truck failure attribute, the technician information, and a location of the vehicle. The truck failure attribute may be a severity of the truck failure. The truck failure is an impeding truck failure and wherein the selection may be based upon an estimated time till an occurrence of the truck failure.

c. Receiving or generating, by the vehicle monitor, repair information about locations and technical skills of multiple shops; and selecting by the vehicle monitor a selected shop based on the shop information and a location of the vehicle. The technical skills of the multiple shops are related to a repair of the truck failure.

d. Receiving or generating, by the vehicle monitor, repair information about locations and technical skills of multiple shops; and selecting by the vehicle monitor a selected shop based on at least one truck failure attribute, the shop information, and a location of the vehicle. The truck failure attribute may be a severity of the truck failure. The truck failure may be an impeding truck failure and wherein the selection is based upon an estimated time till an occurrence of the truck failure.

Figure 25:
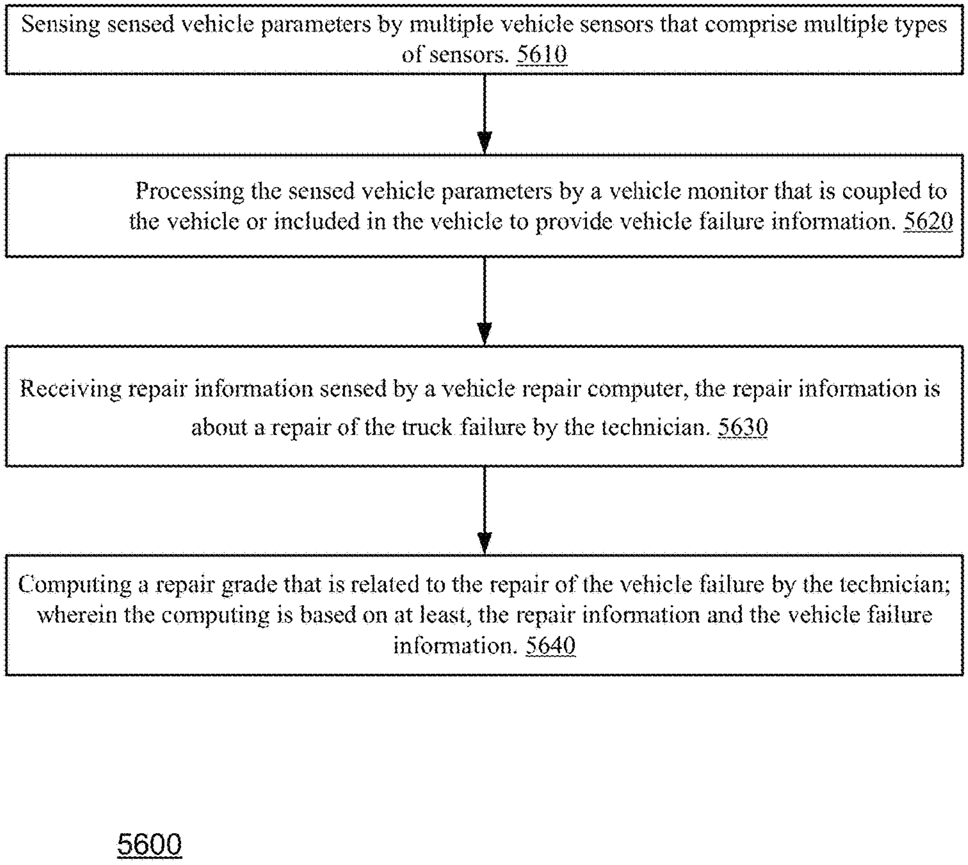
FIG. 25 illustrates a method according to an embodiment of the invention.

FIG. 25 illustrates method 5600 according to an embodiment of the invention.

Method 5600 may be used for grading a technician.

Method 5600 may include the following steps:

Step 5610 of sensing sensed vehicle parameters by multiple vehicle sensors that comprise multiple types of sensors.

Step 5620 of processing the sensed vehicle parameters by a vehicle monitor that is coupled to the vehicle or included in the vehicle to provide vehicle failure information.

Step 5630 of receiving repair information sensed by a vehicle repair computer, the repair information is about a repair of the truck failure by the technician.

Step 5640 of computing a repair grade that is related to the repair of the vehicle failure by the technician; wherein the computing is based on at least, the repair information and the vehicle failure information.

Step 5640 may include computing of the repair grade in response to repairs of the same vehicle failure by other technicians.

The invention may also be implemented in a computer program for running on a computer system, at least including code portions for performing steps of a method according to the invention when run on a programmable apparatus, such as a computer system or enabling a programmable apparatus to perform functions of a device or system according to the invention.

The computer program may cause the storage system to allocate disk drives to disk drive groups.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc. A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system. The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms “front,” “back,” “top,” “bottom,” “over,” “under” and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively “associated” such that the desired functionality is achieved. Hence, any two components herein combined to achieve a particular functionality may be seen as “associated with” each other such that the desired functionality is achieved, irrespective of architectures or intermedial components. Likewise, any two components so associated can also be viewed as being “operably connected,” or “operably coupled,” to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, and other embedded systems, cell phones and various other wireless devices, commonly denoted in this application as ‘computer systems’.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word ‘comprising’ does not exclude the presence of other elements or steps then those listed in a claim. Furthermore, the terms “a” or “an,” as used herein, are defined as one or more than one. Also, the use of introductory phrases such as “at least one” and “one or more” in the claims should not be construed to imply that the introduction of another claim element by the indefinite articles “a” or “an” limits any particular claim containing such introduced claim element to inventions containing only one such element, even when the same claim includes the introductory phrases “one or more” or “at least one” and indefinite articles such as “a” or “an.” The same holds true for the use of definite articles. Unless stated otherwise, terms such as “first” and “second” are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for failure analysis, the method comprises:
- sensing sensed vehicle parameters by multiple vehicle sensors that comprise multiple types of sensors;
- calculating, by a vehicle monitor, based on the sensed vehicle parameters, parameters of multiple vehicle components; wherein the vehicle monitor is mechanically coupled to the vehicle or installed in the vehicle;
- searching, by the vehicle monitor and based on the parameters of the multiple vehicle components, for a vehicle failure that is either a current vehicle failure or an impeding vehicle failure;
- receiving, by the vehicle monitor, a notification that the vehicle failure was repaired; and
- estimating a success of the repair by the vehicle monitor and based on at least parameters of multiple vehicle components that are calculated from sensed vehicle parameters that are sensed after the repair.

2. The method according to claim 1 comprising transmitting a report about the impact of the repair to a computer located outside the vehicle.

3. The method according to claim 1 wherein the estimating comprises comparing between a status of the vehicle before the repair and a status of the vehicle after the repair.

4. The method according to claim 1 comprising receiving or generating, by the vehicle monitor, repair information about locations and technical skills of multiple technicians; and selecting by the vehicle monitor a selected technician based on the repair information and a location of the vehicle.

5. The method according to claim 4 wherein the technical skills of the multiple technicians are related to a repair of the vehicle failure.

6. The method according to claim 1 comprising receiving or generating, by the vehicle monitor, repair information about locations and technical skills of multiple technicians; and selecting by the vehicle monitor a selected technician based on at least one vehicle failure attribute, the repair information and a location of the vehicle.

7. The method according to claim 6 wherein the vehicle failure attribute is a severity of the vehicle failure.

8. The method according to claim 6 wherein the vehicle failure is an impeding vehicle failure and wherein the selection is based upon an estimated time till an occurrence of the vehicle failure.

9. The method according to claim 1 comprising receiving or generating, by the vehicle monitor, repair information about locations and technical skills of multiple shops; and selecting by the vehicle monitor a selected shop based on the repair information and a location of the vehicle.

10. The method according to claim 9 wherein the technical skills of the multiple shops are related to a repair of the vehicle failure.

11. The method according to claim 1 comprising receiving or generating, by the vehicle monitor, repair information about locations and technical skills of multiple shops; and selecting by the vehicle monitor a selected shop based on at least one vehicle failure attribute, the repair information and a location of the vehicle.

12. The method according to claim 11 wherein the vehicle failure attribute is a severity of the vehicle failure.

13. The method according to claim 11 wherein the vehicle failure is an impeding vehicle failure and wherein the selection is based upon an estimated time till an occurrence of the vehicle failure.

14. The method according to claim 1 comprising receiving or generating, by the vehicle monitor, repair information about locations and technical skills of multiple technicians; and suggesting to a driver of the vehicle a selected technician based on at least one vehicle failure attribute, the repair information and a location of the vehicle.

15. A computer program product that is non-transitory and stores instructions that once executed by a vehicle monitor causes the vehicle monitor to perform the steps of:
- receiving sensed vehicle parameters that are sensed by multiple vehicle sensors that comprise multiple types of sensors;
- calculating based on the sensed vehicle parameters, parameters of multiple vehicle components; wherein the vehicle monitor is mechanically coupled to the vehicle or installed in the vehicle;
- searching, based on the parameters of the multiple vehicle components, for a vehicle failure that is either a current vehicle failure or an impeding vehicle failure;
- receiving a notification that the vehicle failure was repaired; and
- estimating a success of the repair by the vehicle monitor and based on at least parameters of multiple vehicle components that are calculated from sensed vehicle parameters that are sensed after the repair.

16. The computer program product according to claim 15 that stores instructions for transmitting a report about the success of the repair to a computer located outside the vehicle.

17. The computer program product according to claim 15 wherein the estimating comprises comparing between a status of the vehicle before the repair and a status of the vehicle after the repair.

18. The computer program product according to claim 15 that stores instructions for receiving or generating repair information about locations and technical skills of multiple technicians; and selecting a selected technician based on the repair information and a location of the vehicle.

19. The computer program product according to claim 18 wherein the technical skills of the multiple technicians are related to a repair of the vehicle failure.

20. A computer program product that is non-transitory and stores instructions that once executed by a computer causes the computer to perform the steps of:

receiving sensed vehicle parameters by multiple vehicle sensors that comprise multiple types of sensors;

processing the sensed vehicle parameters to provide vehicle failure information;

receiving repair information sensed by a vehicle repair computer, the repair information is about a repair of the vehicle failure by the technician;

computing a repair grade that is related to the repair of the vehicle failure by a technician; wherein the computing is based on at least, the repair information and the vehicle failure information.

21. The computer program product according to claim 18 that stores instructions for receiving or generating repair information about locations and technical skills of multiple technicians; and selecting a selected technician or a selected shop based on at least one vehicle failure attribute, the repair information and a location of the vehicle.

22. The computer program product according to claim 21 wherein the vehicle failure attribute is a severity of the vehicle failure.

23. The computer program product according to claim 21 wherein the vehicle failure is an impeding vehicle failure and wherein the selection is based upon an estimated time till an occurrence of the vehicle failure.

24. The computer program product according to claim 15 that stores instructions for receiving or generating repair information about locations and technical skills of multiple technicians; and suggesting to a driver of the vehicle a selected technician or a selected shop based on at least one vehicle failure attribute, the repair information and a location of the vehicle.

* * * * *